(12) United States Patent
Abou El Kheir

(10) Patent No.: US 10,765,306 B2
(45) Date of Patent: Sep. 8, 2020

(54) ADVANCED 3-DIMENSIONAL ENDOSCOPIC SYSTEM WITH REAL DYNAMIC CONVERGENCE

(71) Applicant: Tarek Ahmed Nabil Abou El Kheir, Salt Lake City, UT (US)

(72) Inventor: Tarek Ahmed Nabil Abou El Kheir, Salt Lake City, UT (US)

( * ) Notice: Subject to any disclaimer, the term of this patent is extended or adjusted under 35 U.S.C. 154(b) by 263 days.

(21) Appl. No.: 15/741,267

(22) PCT Filed: Jul. 29, 2015

(86) PCT No.: PCT/US2015/042585
§ 371 (c)(1),
(2) Date: Dec. 31, 2017

(87) PCT Pub. No.: WO2017/019049
PCT Pub. Date: Feb. 2, 2017

(65) Prior Publication Data
US 2018/0184887 A1    Jul. 5, 2018

(51) Int. Cl.
*A61B 1/00* (2006.01)
*A61B 1/05* (2006.01)
(Continued)

(52) U.S. Cl.
CPC ...... *A61B 1/00183* (2013.01); *A61B 1/00006* (2013.01); *A61B 1/0008* (2013.01);
(Continued)

(58) Field of Classification Search
None
See application file for complete search history.

(56) References Cited

U.S. PATENT DOCUMENTS 5,305,121 A * 4/1994 Moll .................. A61B 1/05
348/45
5,381,784 A * 1/1995 Adair ................ A61B 1/00193
600/166

(Continued)

OTHER PUBLICATIONS

PCT/US2015/042585; Written Opinion of the International Searching Authority.

*Primary Examiner* — Timothy J Neal
(74) *Attorney, Agent, or Firm* — Edwin Tarver

(57) ABSTRACT

An improved endoscopic device for obtaining 3-dimensional human vision simulated imaging with real dynamic convergence in therapeutic, diagnostic, and other applications. Imaging probes are mounted on a tubular shaft and a simple/sleek slider moves back-and-forth on the shaft, with slider movement optionally modified and redirected to affect imaging probe convergence/divergence. Imaging probe convergence/divergence can be optionally manual for visual target selection, and the probe arms upon which the imaging probes are mounted may also be moved through a combined 180 degree movement range using a manual control. The first and second movement transmitting means respectively adapted to cause slider-initiated convergence, or manual convergence, of the imaging probes each share at least one integrated movement element with the control means adapted for engaging and disengaging the first and second movement transmitting means. The endoscope can be fitted with different diagnostic and therapeutic systems, and can be adapted to work with robotic systems.

20 Claims, 22 Drawing Sheets

(51) Int. Cl.
*A61B 1/313* (2006.01)
*A61B 1/12* (2006.01)

(52) U.S. Cl.
CPC ........ *A61B 1/0016* (2013.01); *A61B 1/00029* (2013.01); *A61B 1/00039* (2013.01); *A61B 1/00096* (2013.01); *A61B 1/00193* (2013.01); *A61B 1/05* (2013.01); *A61B 1/051* (2013.01); *A61B 1/12* (2013.01); *A61B 1/313* (2013.01); *A61B 1/3132* (2013.01)

(56) References Cited

U.S. PATENT DOCUMENTS

| | | | | |
|---|---|---|---|---|
| 5,459,605 | A * | 10/1995 | Kempf | A61B 1/00165 |
| | | | | 359/462 |
| 5,538,497 | A * | 7/1996 | Hori | A61B 1/00096 |
| | | | | 385/117 |
| 5,743,846 | A | 4/1998 | Takahashi et al. | |
| 6,384,968 | B1 | 5/2002 | Ito et al. | |
| 2005/0234296 | A1* | 10/2005 | Saadat | A61B 1/0008 |
| | | | | 600/129 |
| 2007/0055219 | A1 | 3/2007 | Whitman et al. | |
| 2007/0265499 | A1 | 11/2007 | Wood et al. | |
| 2008/0027279 | A1 | 1/2008 | Abou El Kheir | |
| 2011/0306832 | A1* | 12/2011 | Bassan | A61B 1/00009 |
| | | | | 600/109 |
| 2014/0303437 | A1* | 10/2014 | Kikuchi | A61B 1/0008 |
| | | | | 600/106 |
| 2014/0350391 | A1 | 11/2014 | Prisco et al. | |
| 2015/0265143 | A1* | 9/2015 | Yoon | A61B 1/00087 |
| | | | | 600/104 |
| 2017/0258536 | A1* | 9/2017 | Yeung | A61B 17/3421 |

* cited by examiner

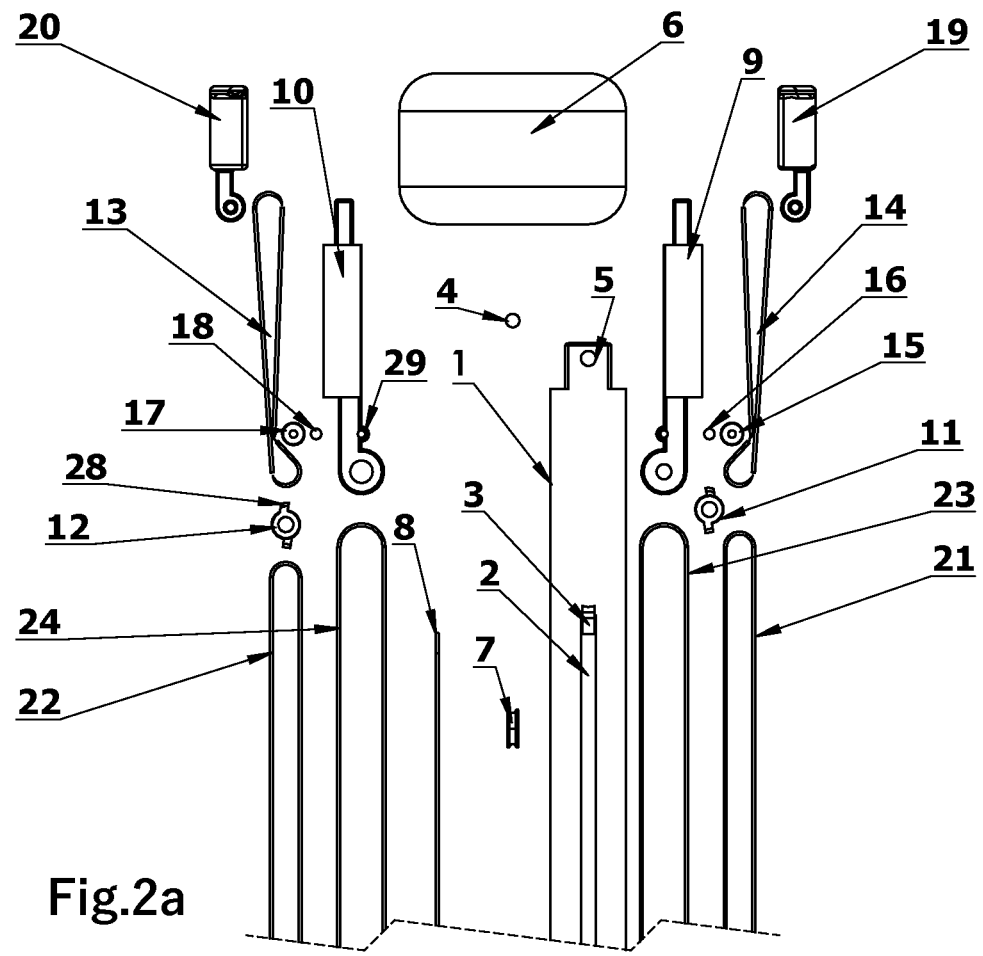
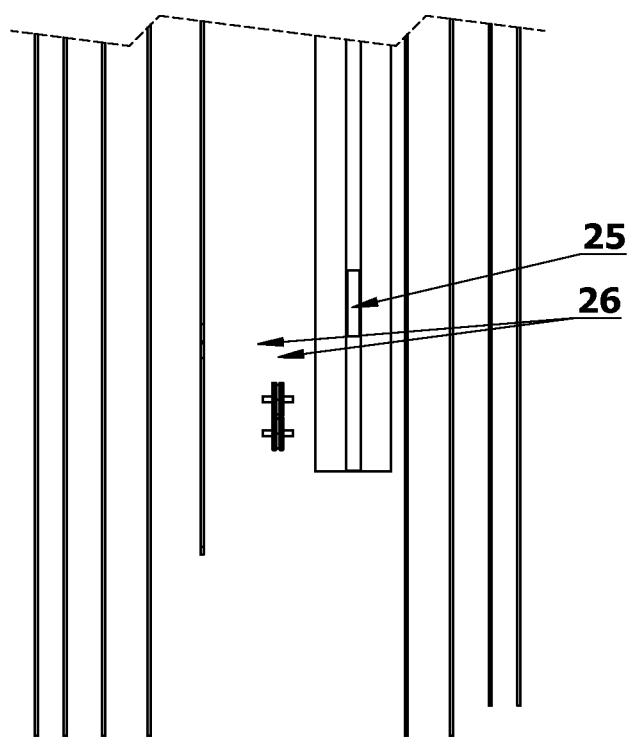
Fig.2a

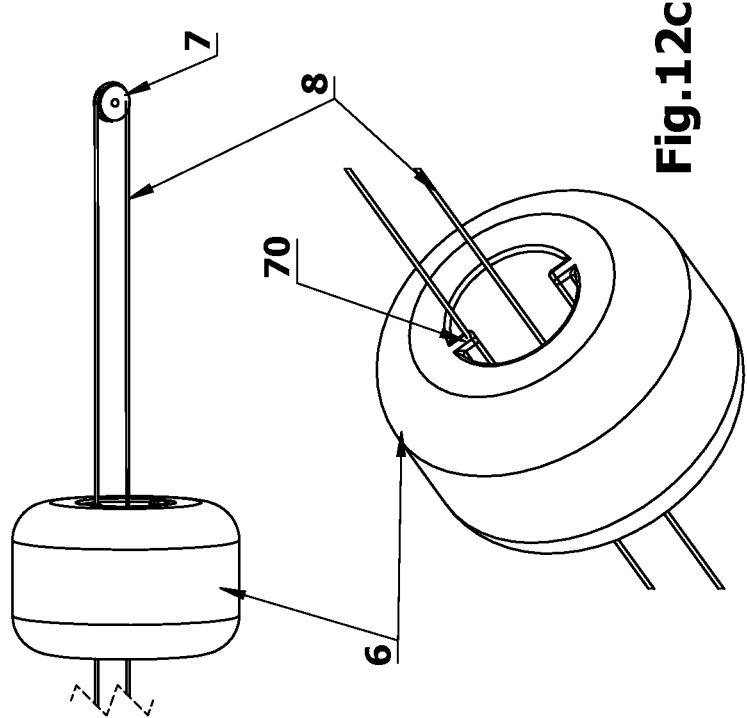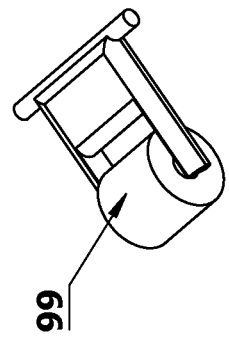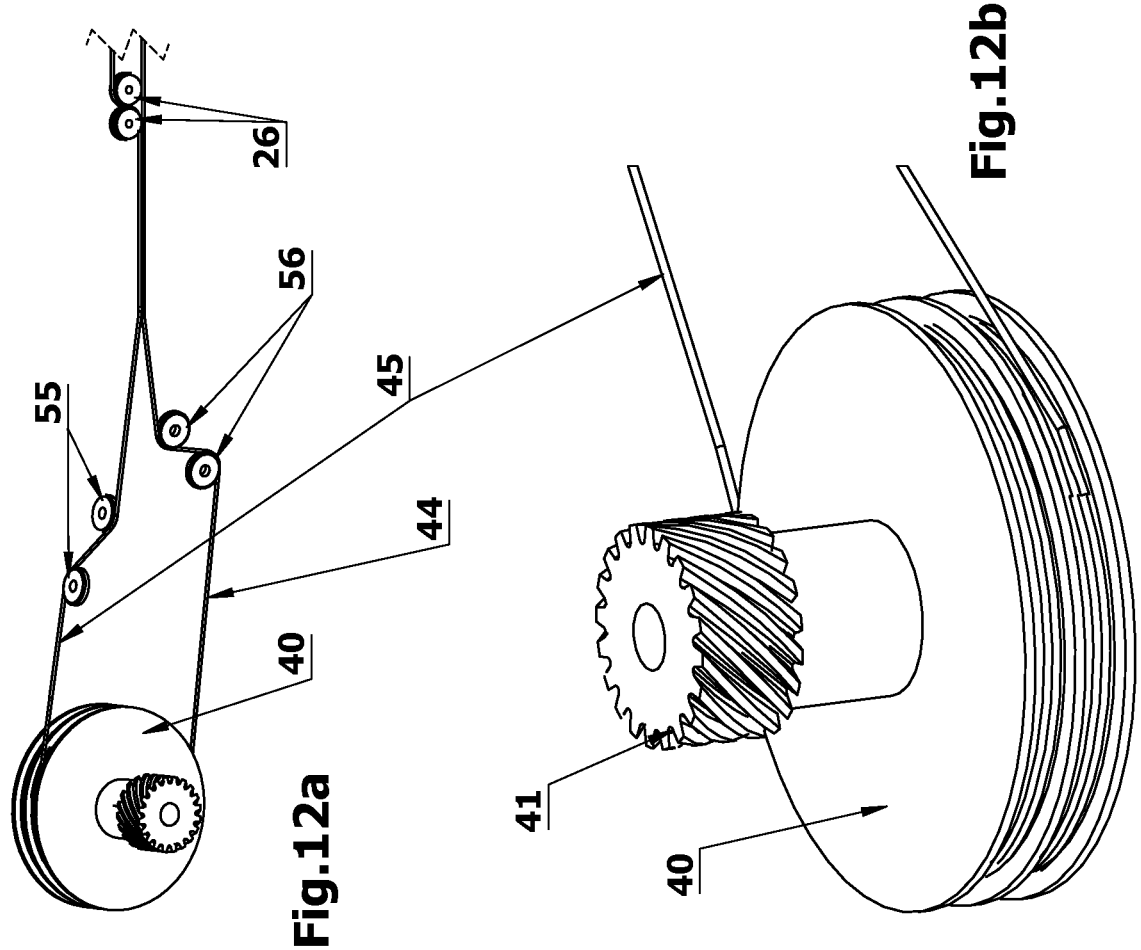

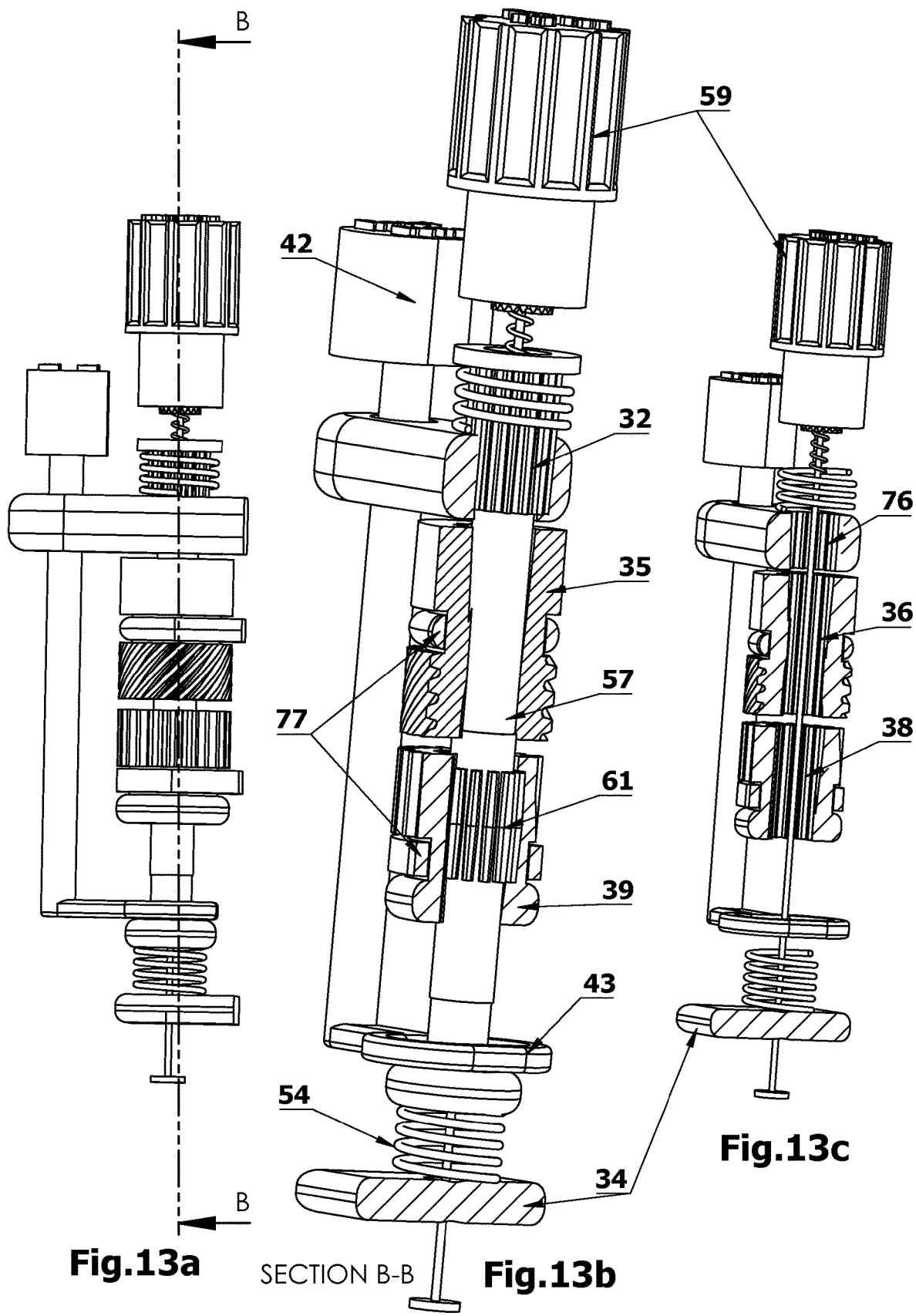

SECTION A-A

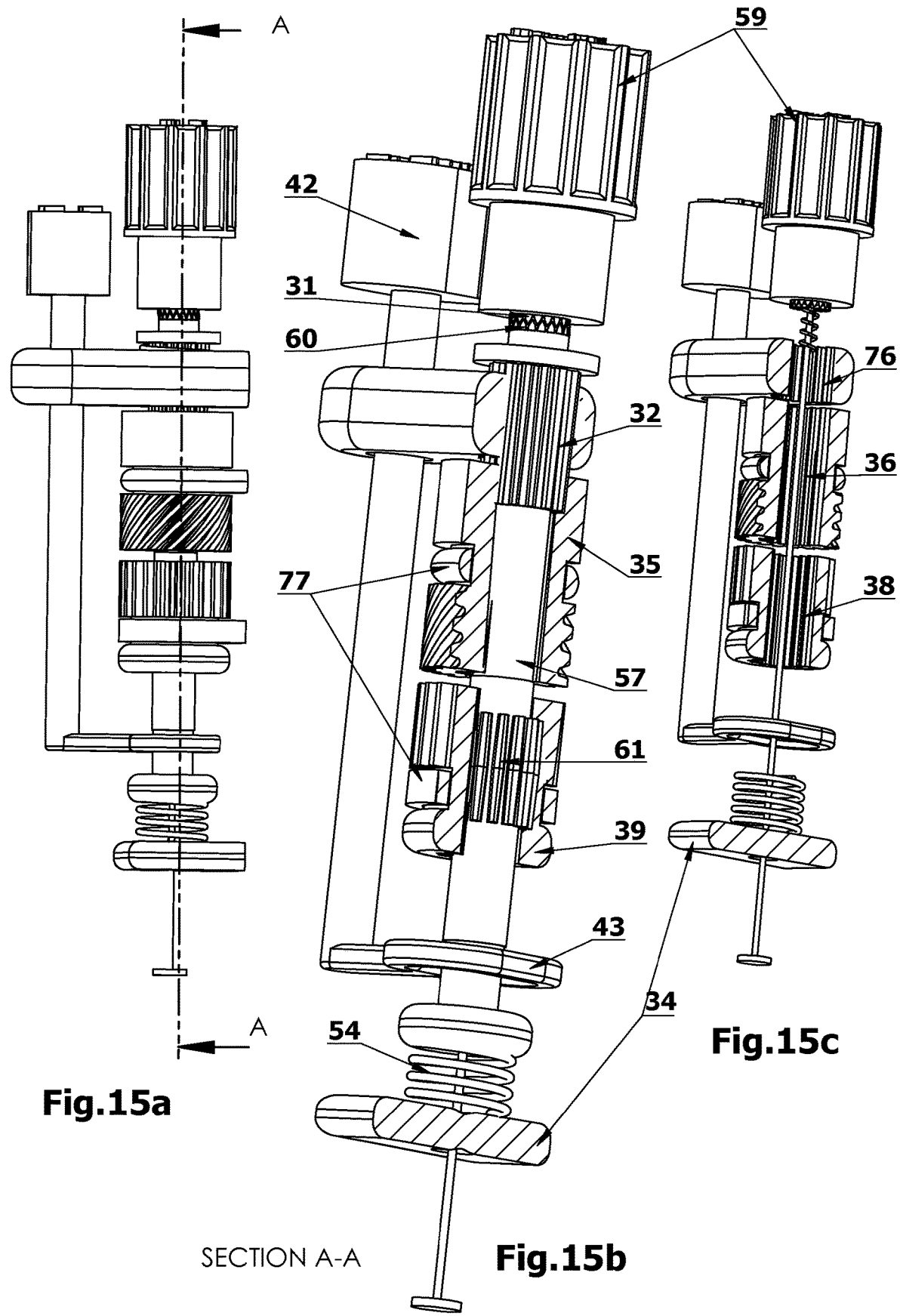

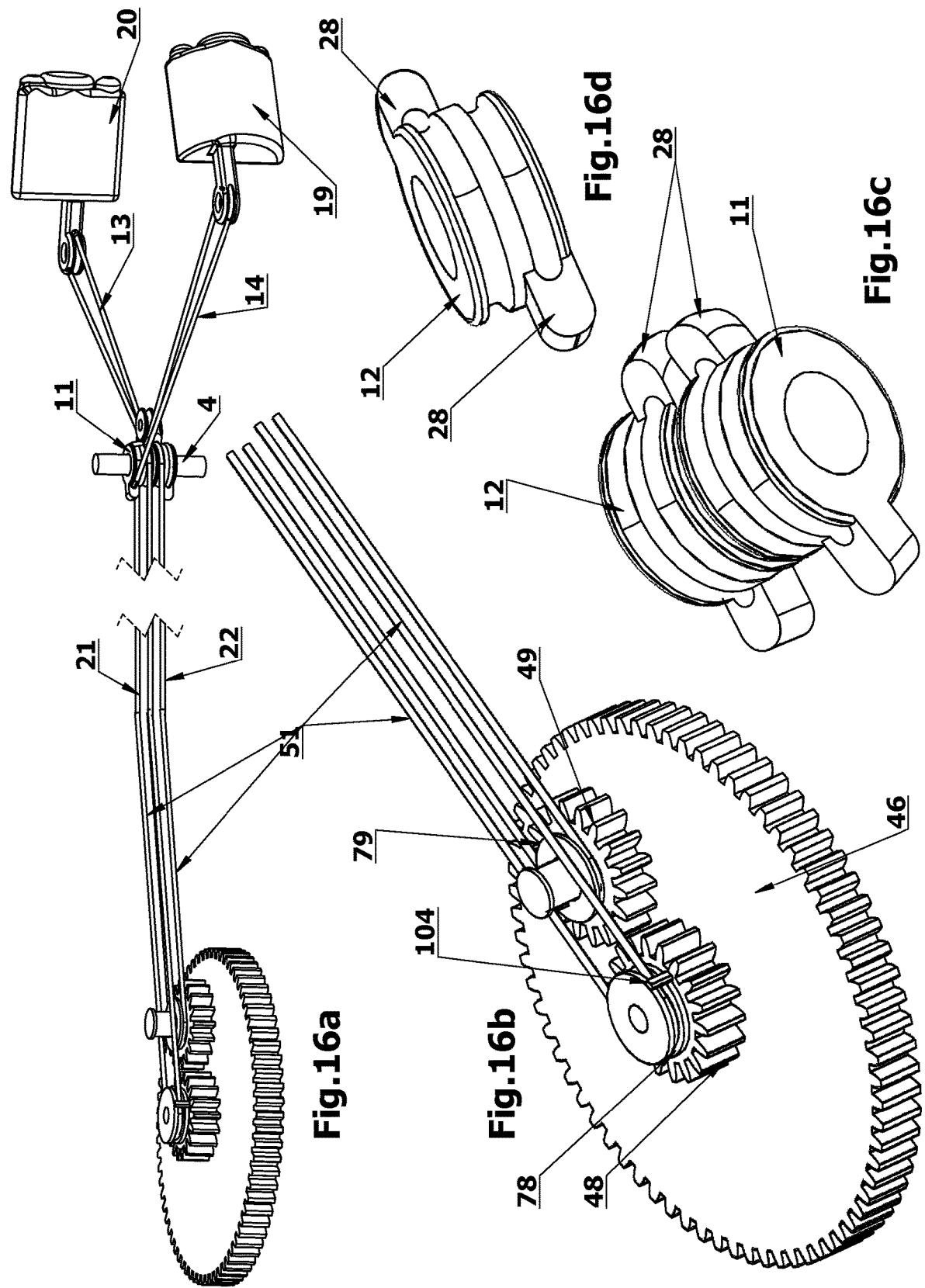

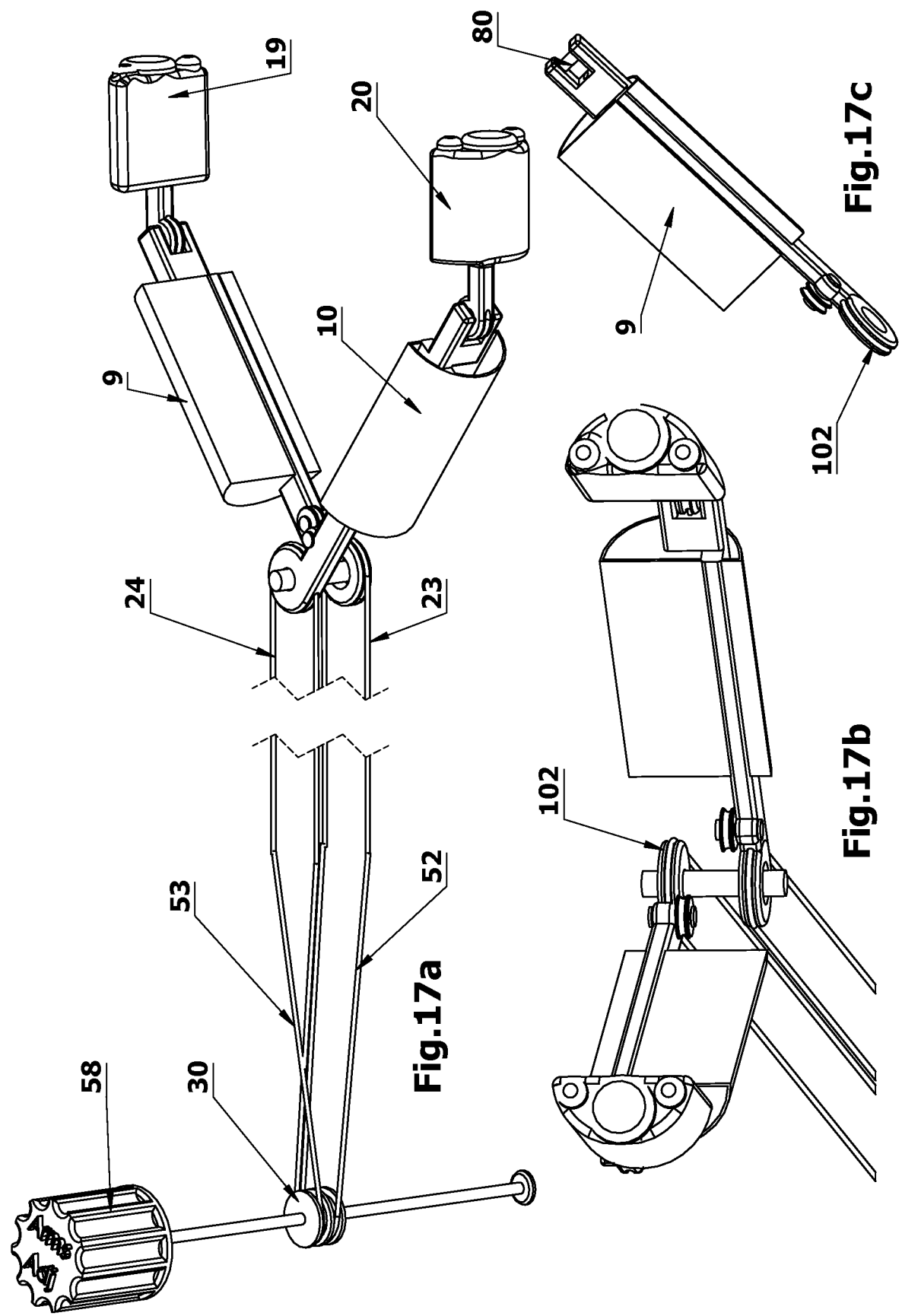

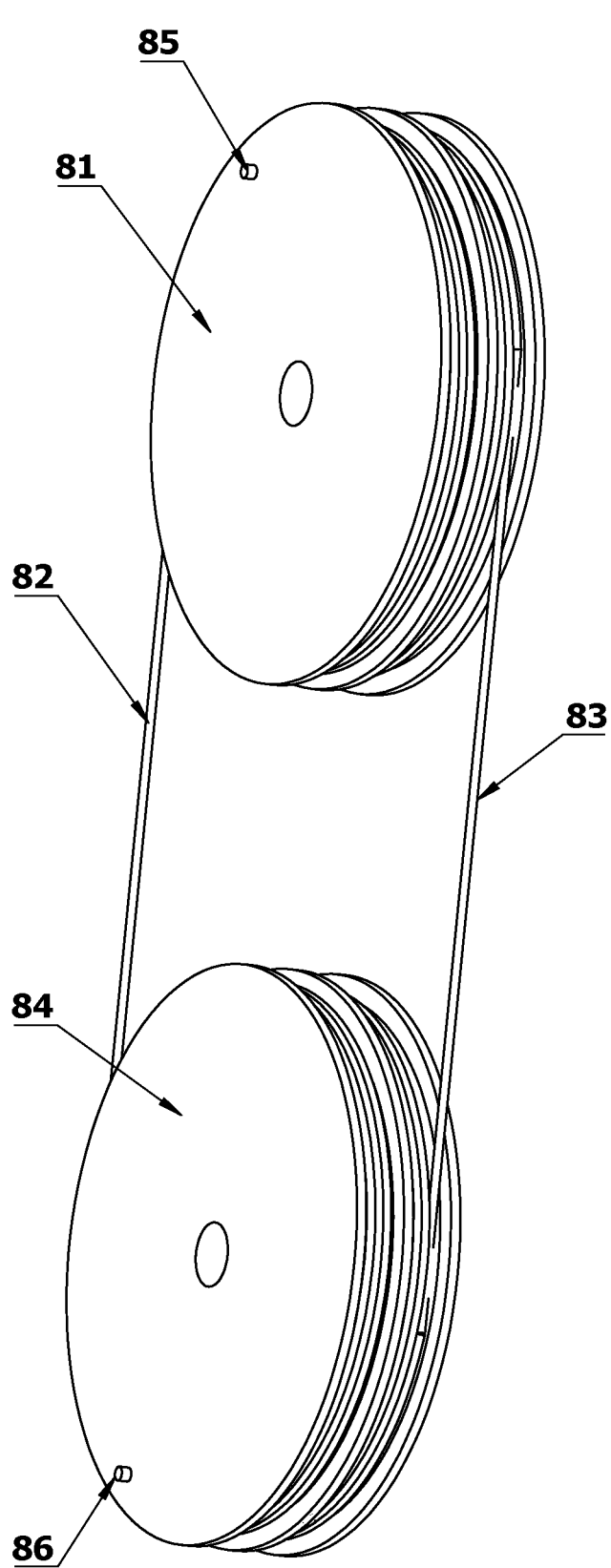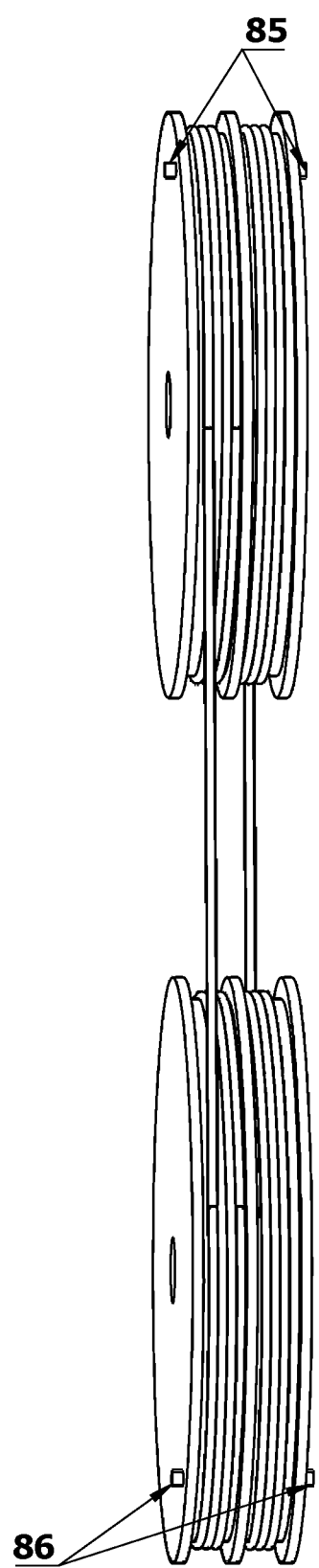
Fig.18a  Fig.18b

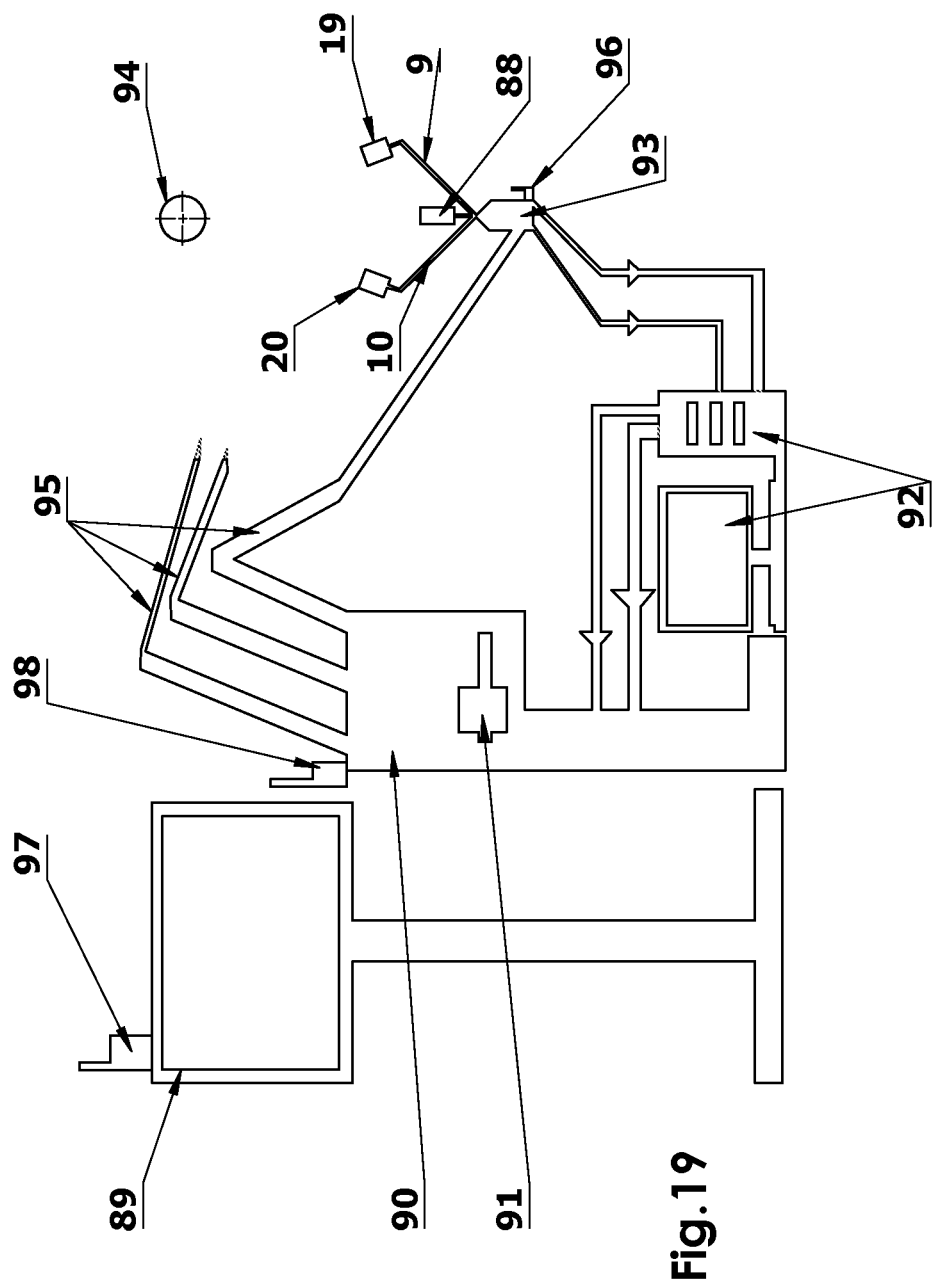

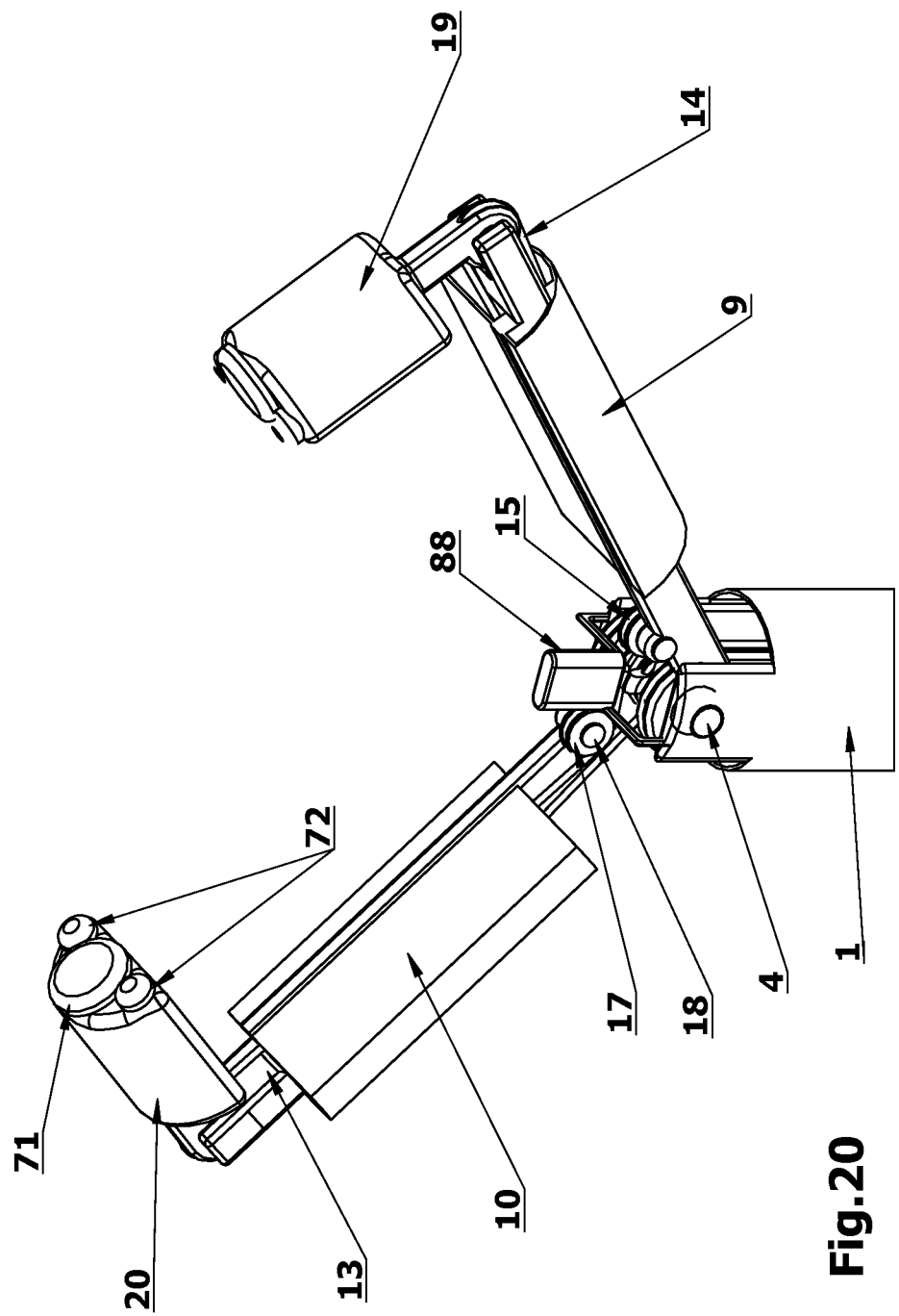

ADVANCED 3-DIMENSIONAL ENDOSCOPIC SYSTEM WITH REAL DYNAMIC CONVERGENCE

RELATED APPLICATIONS

This application claims the benefit of the priority filing date of PCT application number PCT/US2015/042585, filed on 29 Jul. 2015, which is incorporated here by reference in its entirety.

BACKGROUND

Technical Field

This invention relates to the field of medical sensor and treatment devices, specifically to an advanced endoscopic system, and methods for its use, that is adaptable for therapeutic applications, as well as sensor/diagnostic operation, and capable of obtaining 3-dimensional human vision simulated imaging with real dynamic convergence, not virtual convergence. It has more simplified construction than comparable prior art devices, fewer external moving parts for enhanced strength and durability, and less exposed parts for easier medical decontamination between uses. It is also lightweight, more user-friendly, and easier to control, with more interior space than comparable prior art devices for electrical cables that allows more diversified use. Although manual embodiments are identified in this invention disclosure, examples will also be given about contemplated robotic and automated operation for many of its functions. Applications of the advanced endoscopic system may include use in any space with a limited-access opening, including but not limited to, intra-abdominal cavities, intra-thoracic cavities, and intra-cranial cavities, as well as non-medical applications, such as but not limited to search/rescue, scientific research, and investigative applications.

The advanced endoscopic system comprises two movable probe arms that turn freely on the same axis toward and away from each other within a 180-degree range of movement from fully closed side-by-side positioning, and the hollow interior of its main tubular shaft provides a pathway for the belts, electrical wiring, and cables needed to transfer power, sensor information, mechanical movement, and other information between a gearbox and the cameras, lights, positioning sensors, and imaging probes that are predominantly mounted on the distal ends of the two moveable probe arms. Movement of probe arms and imaging probes can be initiated using rotatable controls on the gearbox, or computer-assisted means. A simple, sleek slider positioned for movement back and forth on the main tubular shaft, provides one source of movement affecting the imaging probes for their convergence or divergence on a visual target. Two or more imaging probes may be used at one time, and when this occurs at least two will be the same kind, with each same kind probe mounted onto a different probe arm. When high level of precision is needed, convergence of imaging probes on a visual target can be achieved via semi-automated or fully automated means. Although not limited thereto, operators of the advanced endoscopic system may view the images produced by its cameras or other imaging probes via a 3-dimensional display device, for example a head mount, wherein each of the operator's eyes is sent the images from the camera and/or other imaging probe mounted on a different probe arm that corresponds to this eye (preferably left camera images are transmitted to the left eye and right camera images are transmitted to the right eye).

Improvements Over Prior Art

This invention is an improvement over the invention disclosed in U.S. Pat. No. 8,105,233 B2 to the same inventor herein (2012), with the present invention advanced endoscopic system being more sophisticated, more user-friendly, less fragile, easier to control, and having fewer external moving parts that reduce contamination risk in medical applications, much of which is attributable to the replacement of the 2012 invention's outer shell, moving cylindrical sheath, and adjustment ring with a simple, sleek slider, or other simple positioning sensor that determines the location of the endoscope in relation to a target object, as well as the direction and amount of its movement toward and away from the target object, which can then be used by a computer component in combination with data collected from an endoscope-to-target distance sensor for automated imaging probe convergence. In addition, movement transmitting means and control means previously supported by the main tubular shaft in the 2012 patent mentioned above, are now reconfigured and housed in the gearbox, unless at least one automated function is present. No other endoscopic system and method adaptable for therapeutic and non-medical applications, as well as sensor/diagnostic operation, is known with the same structure as the present invention, to provide all of its benefits and advantages, and/or function in the same manner as the present invention to provide real dynamic convergence flexibility in spaced-apart probe distance adjustment that facilitates imaging probe use in a larger variety of applications and in different types of cavities or spaces while simultaneously giving its operator superior depth perception.

SUMMARY

The primary object of this invention is to provide an endoscopic system and method that is capable of obtaining 3-dimensional human vision simulated imaging with real dynamic convergence, and which is also adaptable for diagnostic/sensor operation, therapeutic applications, and other applications involving a limited access visual target. Another object of this invention is to provide an endoscopic system that is more sophisticated than prior art inventions, more user-friendly, less fragile, easier to control, and has fewer external moving parts for reduced contamination risk. It is also an object of this invention to provide an endoscopic system that is durably constructed and made from materials able to withstand without premature deterioration the repeated sanitizing procedures required for body cavity insertions.

The present invention, when properly made and used, provides an improved endoscopic system and method for obtaining 3-dimensional human vision simulated imaging with real dynamic convergence in therapeutic, diagnostic, and other applications. Its imaging probes are mounted on freely movable probe arms attached to the distal end of a main tubular shaft, and a simple, sleek slider (or other positioning sensor) moves back-and-forth on the shaft. This movement can be modified and redirected to the imaging probes for their convergence or divergence. However, for visual target selection, imaging probe convergence/divergence is optionally manual via a control associated with its gearbox. Probe arm movement through a combined 180-degree range movement can also be manually activated through use of a gearbox control. The first and second movement transmitting means respectively adapted to cause slider-initiated convergence of the imaging probes, or manual convergence thereof, each share at least one integrated movement element with the control means adapted for engaging and disengaging the first and second movement transmitting means. Furthermore, the present invention endoscopic system can be fitted with a wide variety of diagnostic and therapeutic systems, a computer can be connected to its gearbox when enhanced precision is required in an application, and the present invention can be adapted to work with robotic systems.

Since the description herein provides preferred embodiments of the present invention, and examples of invention structure and use, it should not be construed as limiting the scope of the present invention. Accordingly, components other than those specifically shown and described herein may be substituted, as long as they are able to effectively fulfill the intended function. Thus, the scope of the present invention should be determined by the appended claims and their legal equivalents, rather than being limited to the specific examples given.

BRIEF DESCRIPTION OF THE FIGURES

FIG. 2a illustrates an exploded view of components in the first and second movement transmitting means of the invention shown in FIG. 1 which relate to slider movement and movement of the imaging probes for convergence and divergence;

FIG. 3 is an enlarged view of the same components shown in the top portion of FIG. 2a;

FIG. 12a is a perspective view of the first movement transmitting means used in the invention shown in FIG. 1;

FIG. 12b is an enlarged view of the large dual groove pulley with helical gear shown in FIG. 12a;

FIG. 12c is an enlarged view of the slider shown in FIG. 12a, with a belt/cable used for slider movement attached to one side of the slider's interior rail assembly;

FIG. 12d is a perspective view a roller that can be used with the slider shown in FIG. 12c to assist its movement along the main tubular shaft or in a channel on the main tubular shaft;

FIG. 13a is a side view of the control means in the gearbox of the invention in FIG. 1 showing the convergence mechanism core rod in its position of use with the first and second movement transmitting means disengaged, and a related reset button supported by a bushing/bracket that is secured to the gearbox backbone, with the reset button in a downwardly depressed position;

FIG. 13b is a sectioned view of the invention structure in FIG. 13a, which shows the external teeth of convergence mechanism core rod only engaging the internal teeth of the imaging probes convergence-related gear, illustrating first and second movement transmitting means disengagement, which further shows the external teeth of the slider-related locking gear disengaged from the internal teeth of slider-related helical gear with external teeth;

FIG. 13c is a sectioned view of the invention structure shown in FIG. 13b, except the convergence mechanism core rod and slider-related locking gear have been removed to reveal the internal teeth in the imaging probes convergence-related gear, in the slider-related helical gear, and also in the bushing/bracket fixed to the gearbox backbone;

FIG. 14a is a side view of the control means in the gearbox of the invention in FIG. 1 showing the convergence mechanism core rod in its position of use with the first and second movement transmitting means engaged, and also showing the related reset button reset button supported by a bushing/bracket that is secured to the gearbox backbone, the reset button now with upward positioning as compared to that shown in FIG. 13a;

FIG. 14b is a sectioned view of the invention structure in FIG. 14a, which shows the external teeth of the convergence mechanism core rod engaging both the internal teeth of the slider-related helical gear with external teeth and the internal teeth of the imaging probes convergence-related gear for first and second movement transmitting means engagement, which further shows the external teeth of the slider-related locking gear disengaged from the internal slider-related helical gear with external teeth;

FIG. 14c is a sectioned view of the invention structure shown in FIG. 14b, except the convergence mechanism core rod and slider-related locking gear have been removed to reveal the internal teeth in the imaging probes convergence-related gear, in the slider-related helical gear, and also in a bushing/bracket fixed to the gearbox backbone;

FIG. 15a is a side view of the control means in the gearbox of the invention in FIG. 1 showing the convergence mechanism core rod in its position of use for manual convergence and with the first and second movement transmitting means disengaged, also showing the slider-related locking gear engaging the slider-related helical gear with external teeth, and further showing the reset button in a downwardly depressed position similar to that in FIG. 13a;

FIG. 15b is a sectioned view of the invention structure in FIG. 15a, which shows the external teeth of convergence mechanism core rod only engaging the internal teeth of imaging probes convergence-related gear and the bottom teeth of convergence adjust button engaging external top teeth of the convergence mechanism core rod for manual convergence, and also shows the slider-related locking gear engaging the slider-related helical gear with external teeth to lock it in place;

FIG. 15c is a sectioned view of the invention structure shown in FIG. 15b, except the convergence mechanism core rod and slider-related locking gear have been removed to reveal the internal teeth in the imaging probes convergence-related gear, in the slider-related helical gear, and also in a bushing/bracket fixed to the gearbox backbone;

FIG. 16a is a perspective view of the second movement transmitting means used in the invention shown in FIG. 1;

FIG. 16b is enlarged view of the large dual gear (larger/smaller gear combination) with pulley assembly that is shown in FIG. 16a, which relates to imaging probes convergence, also showing a small diameter gear with pulley associated with the smaller gear in dual gear, with pulley assembly;

FIG. 16c is a perspective view of a pair of dual groove pulleys with cable crimp sleeves usable as a part of the invention in FIG. 1 to fix cables/belts to their corresponding pulleys;

FIG. 16d is a perspective view of a single dual groove pulley with cable crimp sleeve usable as a part of the invention in FIG. 1 and similar to the pair of dual groove pulleys shown in FIG. 16c;

FIG. 17a is a perspective view of the third movement transmitting means used in the invention shown in FIG. 1;

FIG. 17b is an enlarged view of the probe arms in FIG. 17a, and also showing the imaging probes connected to the probe arms having parallel positioning with respect to one another, providing a non-converged configuration;

FIG. 17c is a perspective view of one of the probe arms in FIG. 17b, which more clearly shows its hinged and pulley-like opposing connective ends;

FIG. 18a is a perspective view of an alternative sturdy, non-slip pulley/cable system that is usable as a part of the most preferred embodiment of the present invention shown in FIG. 1;

FIG. 18b is a side view of the pulley/cable system in FIG. 18a;

FIG. 19 is a schematic view of the invention in FIG. 1 during use in a medical application; and FIG. 20 is an enlarged view of the probe arms similar to that in FIGS. 4 and 17a, showing the imaging probes in a converged configuration and not parallel to one another, and also showing a unit fixed to the end of the main tubular shaft between the opened probe arms that can be used as a laser pointer, a endoscope-to-target distance sensor, or to serve another useful function;

DETAILED DESCRIPTION

The following description is presented to enable any person skilled in the art to make and use the invention, and is provided n the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

LIST OF COMPONENTS

Figure 10:
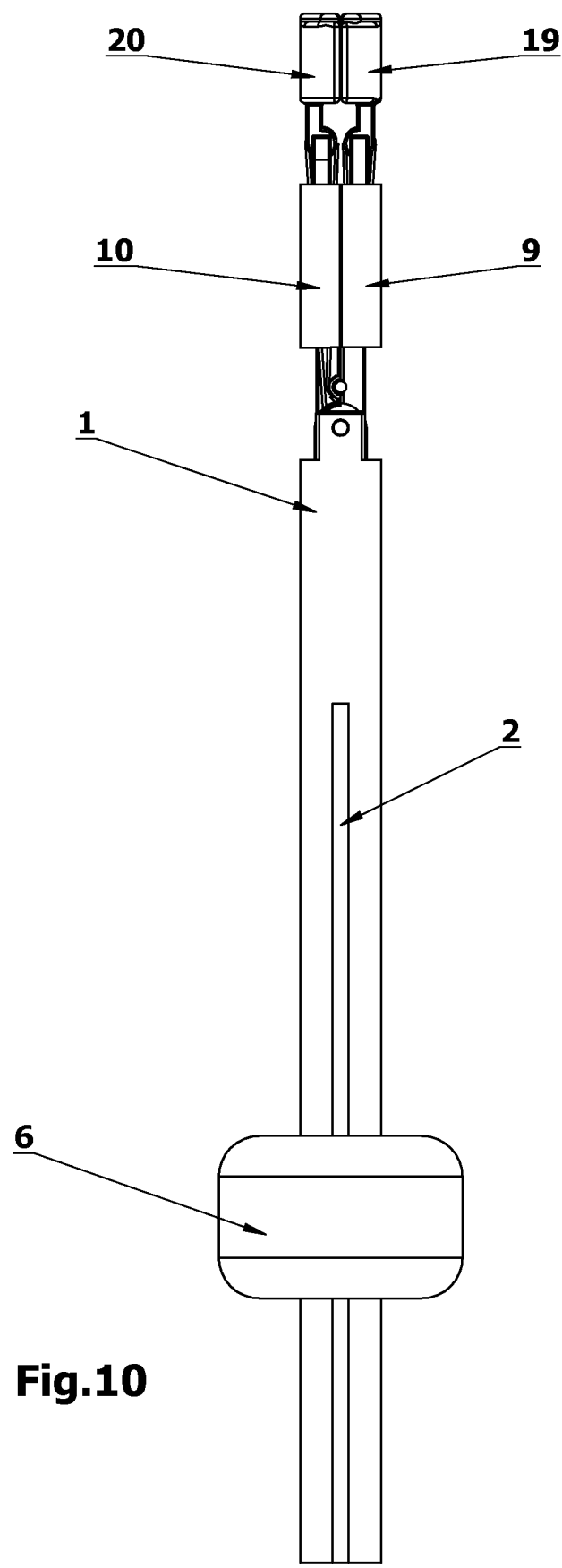
FIG. 10 is an enlarged side view of the same components shown in the top portion of FIG. 1, with probe arms unopened and the imaging probes having side-by-side closed positioning.

1. Main tubular shaft [see FIG. 1, Sheet 1/22; FIG. 2a, Sheet 2/22; FIGS. 3-7, respectively on Sheet 5-9/22; FIG. 10, Sheet 12/22; and FIG. 20, Sheet 22/22]

Figure 2B:
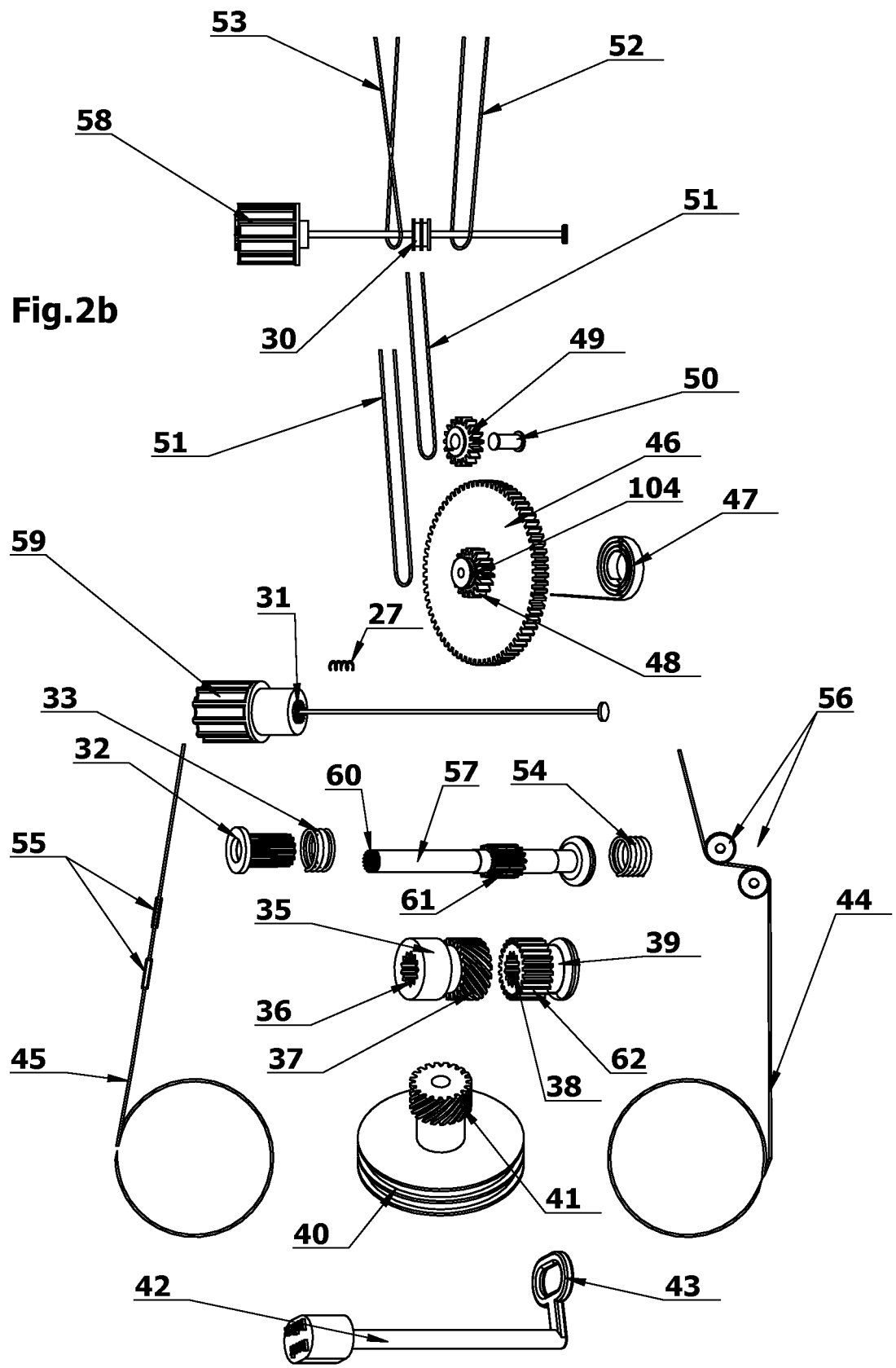
FIG. 2b is an exploded view of components in the first and second movement transmitting means of the invention shown in FIG. 1 which relate to gearbox movement reduction and imaging probes convergence/divergence.
Figure 3:
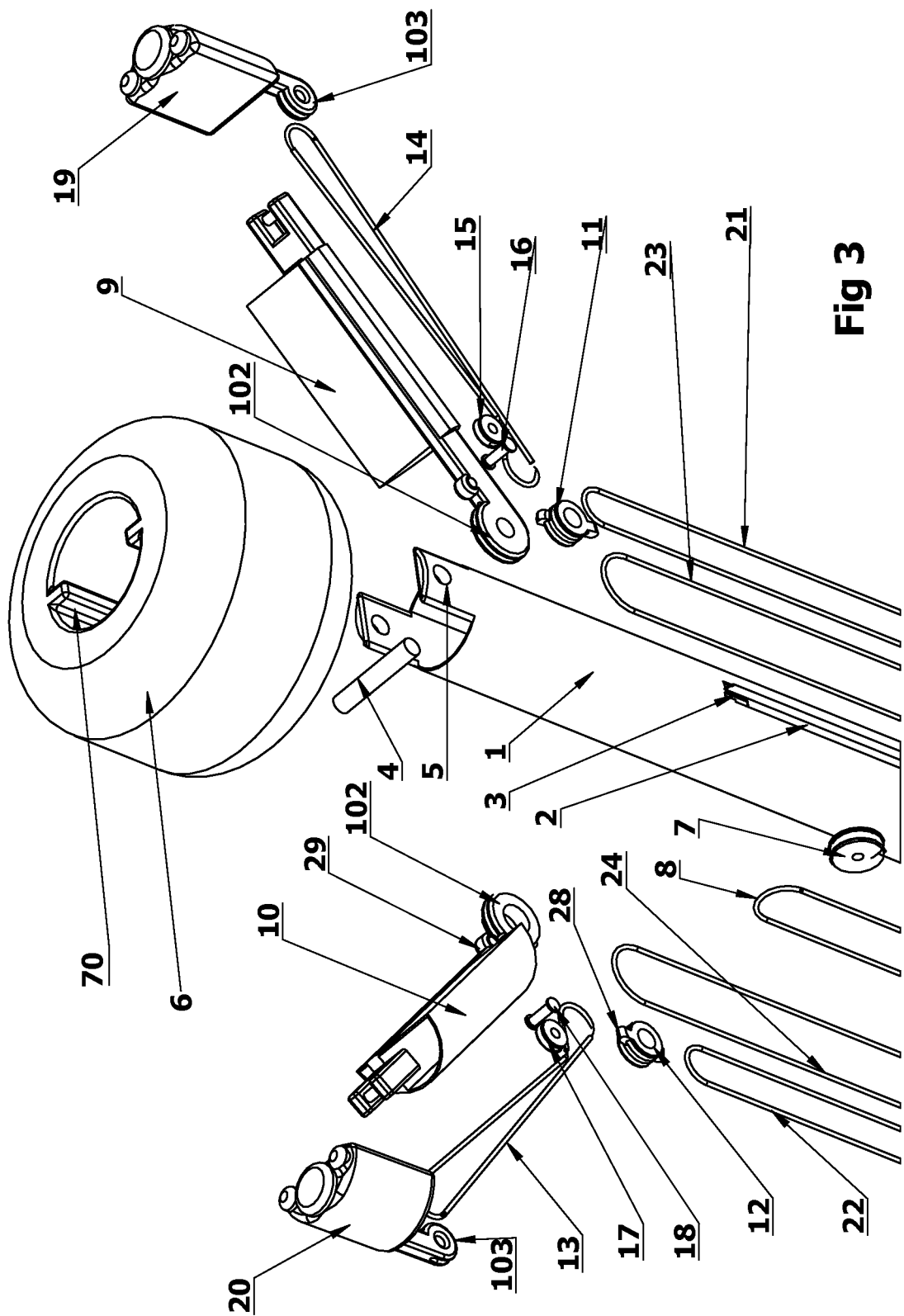

2. At least one longitudinal channel in the exterior surface of the main tubular shaft (#1), which can guide the movement of slider (#6) and can also represent at least part of a positioning sensor for determining the position of the endoscope (#93) in relation to its surroundings and the direction and amount of its movement which may be used by a computer component (#92) along with data collected from endoscope-to-target distance sensor (#88) for automated imaging probe convergence [see FIG. 1, Sheet 1/22; FIG. 2a, Sheet 2/22; FIG. 3, Sheet 5/22; and FIG. 10, Sheet 12/22]

3. Opening in the distal end of one of the two longitudinal channels (#2) on main tubular shaft (#1) allowing entry into main tubular shaft (#1) of the slider cable/belt (#8) [see FIG. 2a, Sheet 2/22; and FIG. 3, Sheet 5/22]

Figure 4:
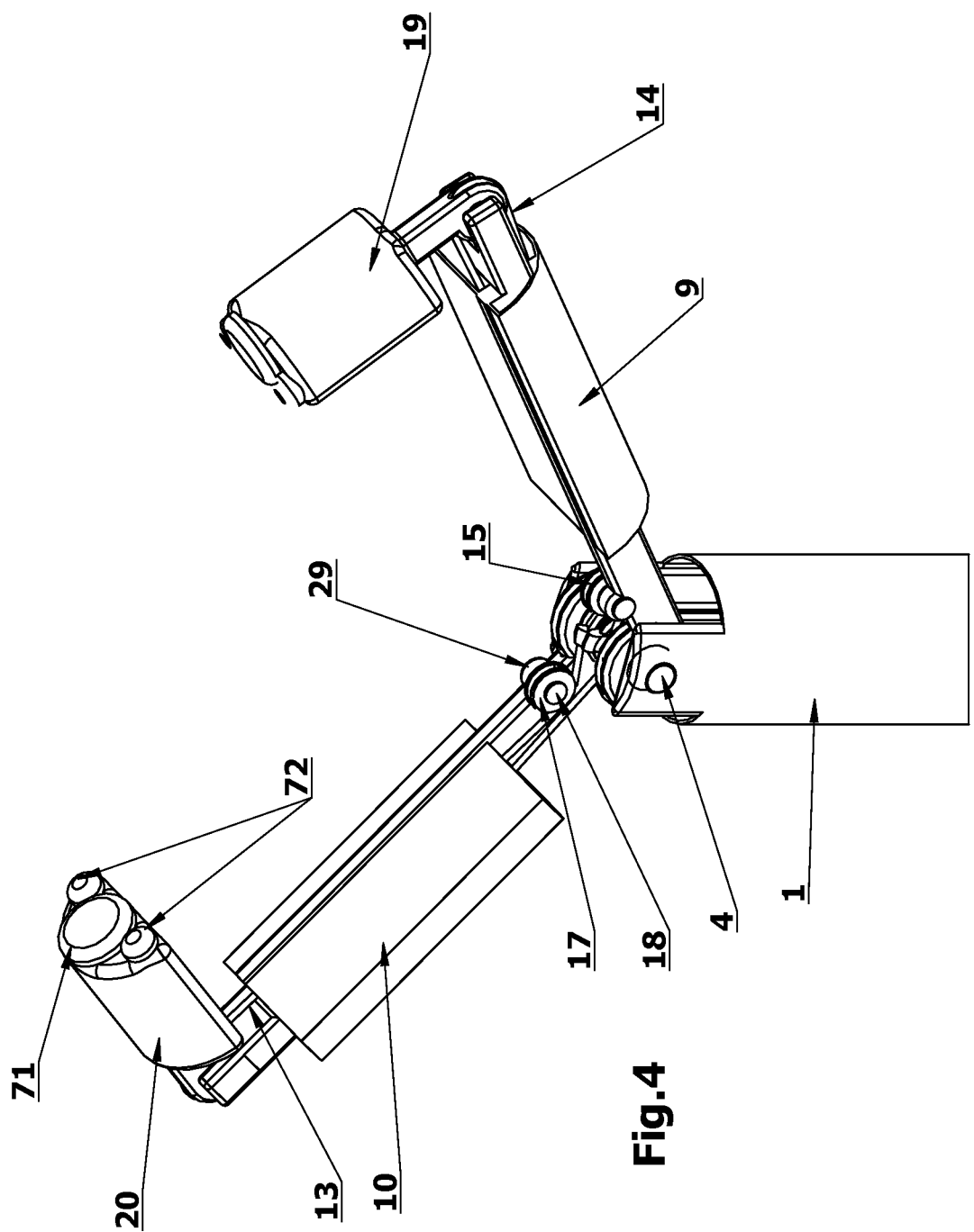
FIG. 4. is a perspective view from the side of the distal end of the invention in FIG. 1, showing the movable connection between the probe arms and the distal end of the main tubular shaft, as well as the movable connection between each imaging probe and the probe arm supporting it, and further with the imaging probes having converged positioning.

4. Pin fixed at the distal end of the main tubular shaft (#1) that engages the probe arms (#9, #10) and can also mount unit (#88) which can be a target-to-device distance sensor, laser pointer, and/or other device/system [see FIG. 2a, Sheet 2/22; FIG. 3, Sheet 5/22; FIG. 4, Sheet 6/22; and FIG. 20, Sheet 22/22]

5. Bore through opposing sides of the distal end of main tubular shaft (#1) where pin (#4) is fixed to movably mount the proximal ends of probe arms (#9, #10) and the dual groove pulleys (#11, #12) that transmit convergence movement to the two imaging probes (#19, #20) supported respectively by probe arms (#9, #10) [see FIG. 2a, Sheet 2/22; and FIG. 3, Sheet 5/22]

Figure 11:
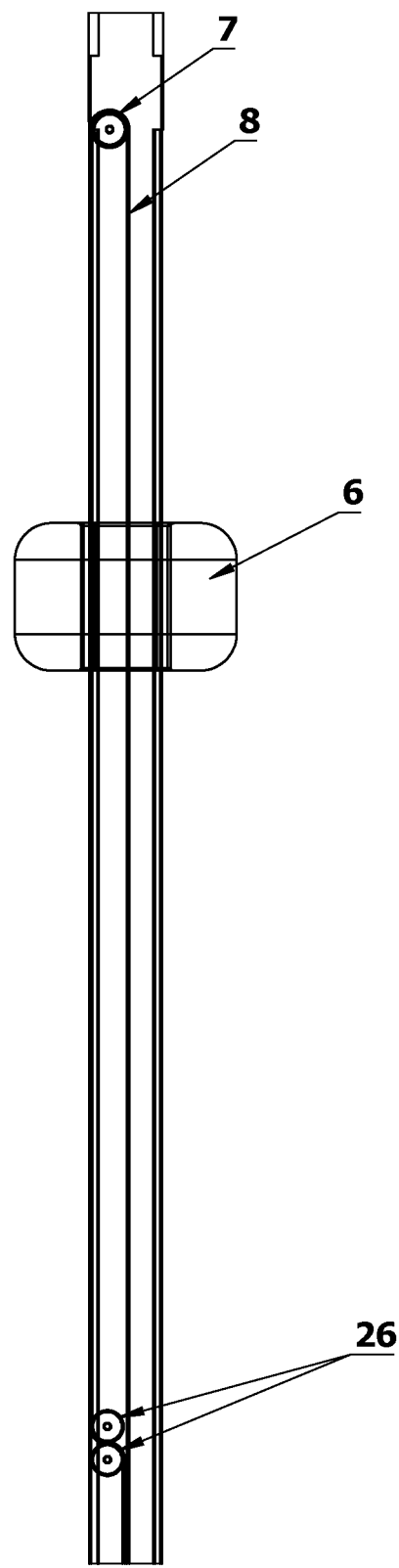
FIG. 11 is a transparent side view of the slider and main tubular shaft in FIG. 10 showing preferred placement of belts/cables and pulleys related to slider movement on the main tubular shaft.

6. Slider that moves smoothly back and forth on and across the exterior surface of main tubular shaft (#1), and can be guided by at least one channel (#2) [see FIG. 1, Sheet 1/22; FIG. 2a, Sheet 2/22; FIG. 3, Sheet 5/22; FIG. 10, Sheet 12/22; FIG. 11, Sheet 13/22; and FIGS. 12a and 12c, Sheet 14]

7. Pulley for slider cable/belt (#8) that is situated within main tubular shaft (#1) close to opening (#3) [see FIG. 2a, Sheet 2/22; FIG. 3, Sheet 5/22; FIG. 11, Sheet 13/22; and FIG. 12a, Sheet 14/22]

8. Slider cable/belt used with slider (#6) and associated with main tubular shaft (#1) and slider (#6) for back and forth movement of slider (#6) on and across the exterior surface of main tubular shaft (#1), with the back and forth movement of slider cable/belt (#8) guided by pulley (#7) and one of the two path guide pulleys (#26) [see FIG. 1, Sheet 1/22; FIG. 2a, Sheet 2/22; FIG. 3, Sheet 5/22; FIGS. 10-11, Sheets 12-13/22; and FIGS. 12a and 12c, Sheet 14/22]

Figure 5:
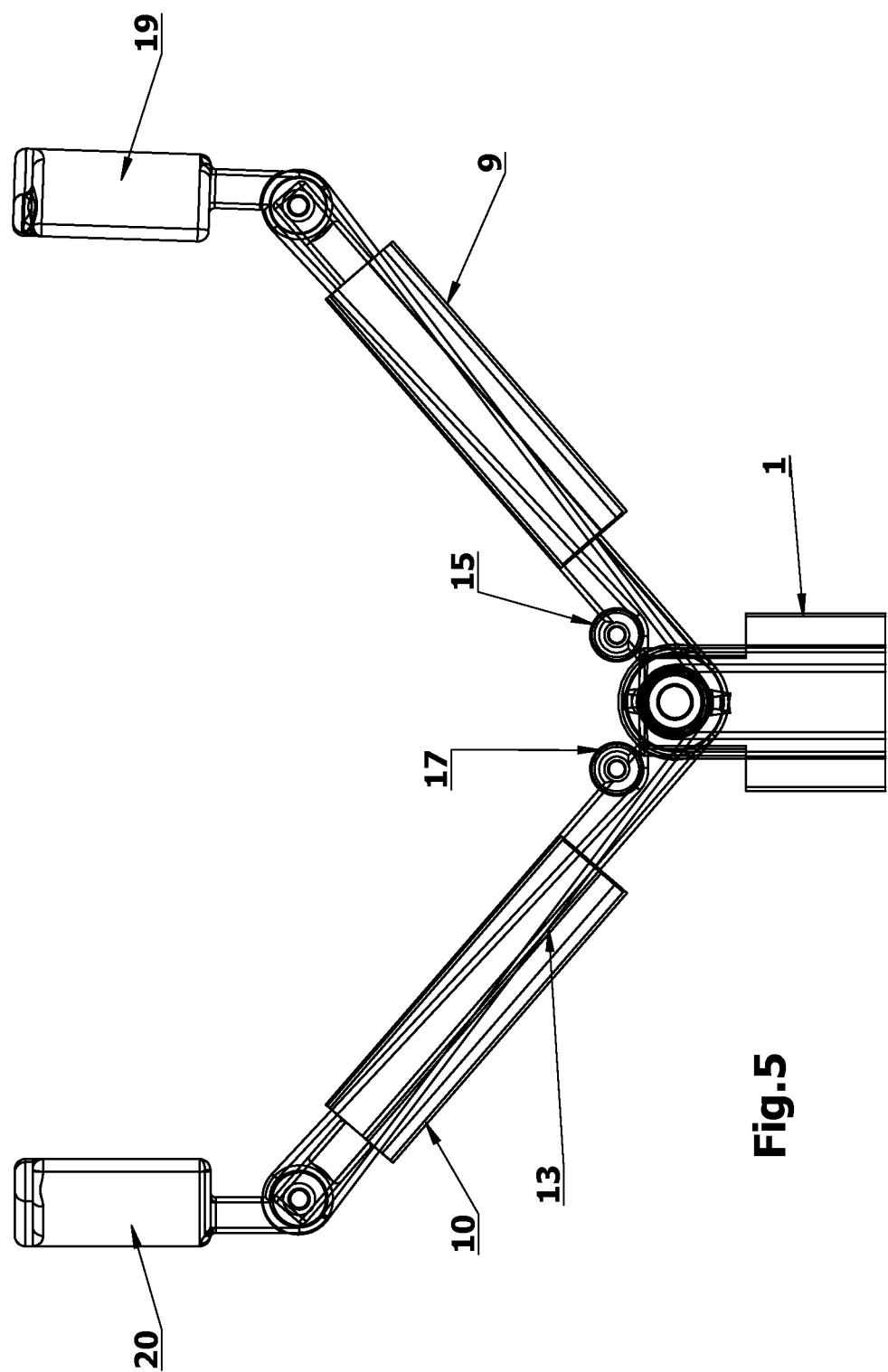
FIG. 5 is a transparent side view of the most preferred embodiment of the present invention that is similar in content to that shown in FIG. 4, with preferred placement of belts/cables and pulleys in the second movement transmitting means now illustrated, and further with the imaging probes in their non-converged neutral positioning.
Figure 9:
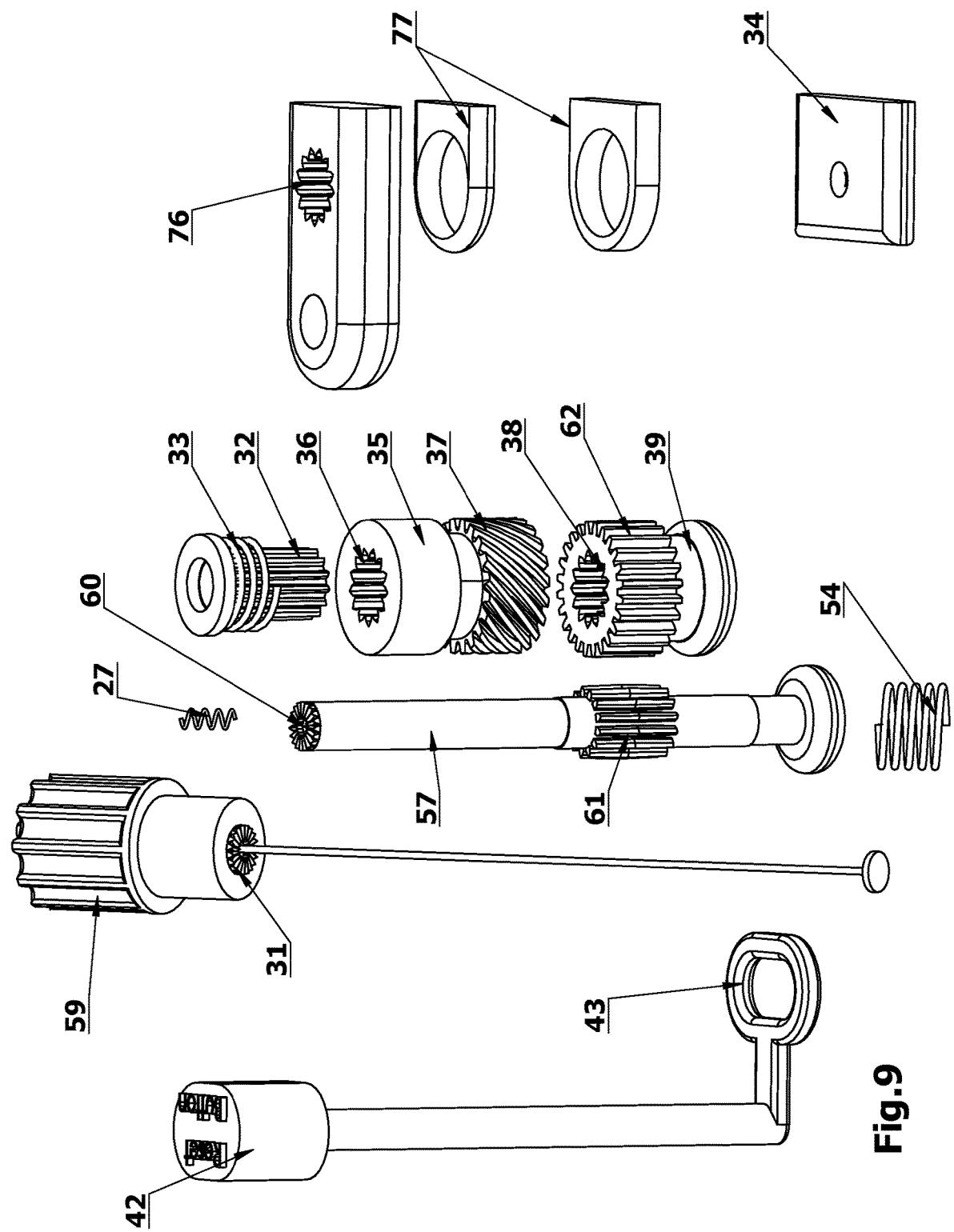
FIG. 9 is an exploded view of components in the gearbox of the invention shown in FIG. 1 that relate to the convergence adjust button with elongated rod that is used for manual convergence of first and second imaging probes during selection of a visual target.

9. First probe arm supporting first imaging probe (#19) and connected by pin (#4) to the distal end of main tubular shaft (#1) [see FIG. 1, Sheet 1/22; FIG. 2a, Sheet 2/22; FIG. 3-5, respectively in Sheet 5-7/22; FIG. 9, Sheet 9/22; FIG. 10, Sheet 12/22; FIGS. 17a and 17b, Sheet 19/22, FIG. 19, Sheet 21/22; and FIG. 20, Sheet 22/22]

10. Second probe arm supporting second imaging probe (#20) and also connected by pin (#4) to the distal end of main tubular shaft (#1) [see FIG. 1, Sheet 1/22; FIG. 2a, Sheet 2/22; FIG. 3-5, respectively in Sheet 5-7/22; FIG. 9, Sheet 9/22; FIG. 10, Sheet 12/22; FIGS. 17a and 17b, Sheet 19/22, FIG. 19, Sheet 21/22; and FIG. 20, Sheet 22/22]

Figure 6:
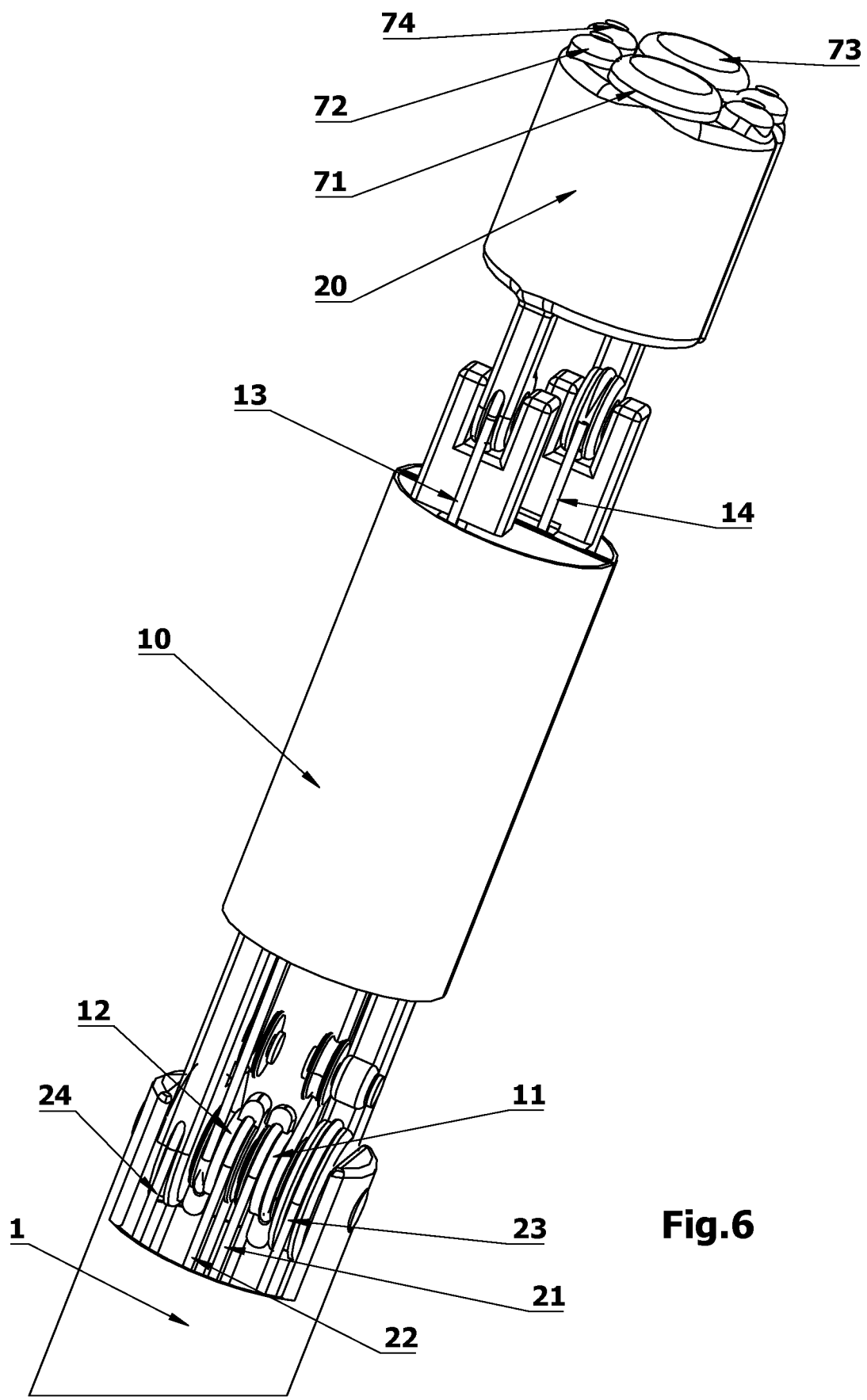
FIG. 6 is a perspective view of the invention similar to FIGS. 4 and 5 showing the connection of the probe arms to the distal end of the main tubular shaft, the connection of the imaging probes to the probe arms, and the probe arms and imaging probes each in their closed positions.

11. First dual groove pulley mounted by pin (#4) adjacent to first probe arm (#9) at the distal end of main tubular shaft (#1) that transmits convergence movement from cable/belt (#21) to the first imaging probe (#19) via engagement with path guide pulley (#15) and first cable/belt (#14) [see FIG. 2a, Sheet 2/22; FIG. 3, Sheet 5/22; FIG. 6, Sheet 8/22; and FIG. 16c, Sheet 18/22]

12. Second dual groove pulley mounted by pin (#4) adjacent to probe arm (#10) at the distal end of main tubular shaft (#1) that transmits convergence movement from cable/belt (#22) to the second imaging probe (#20) via engagement with path guide pulley (#17) and second cable/belt (#13) [see FIG. 2a, Sheet 2/22; FIG. 3, Sheet 5/22; FIG. 6, Sheet 8/22; and FIGS. 16a, 16c, and 16d, Sheet 18/22]

13. Second cable/belt for transmitting convergence movement to second imaging probe (#20) [see FIG. 2a, Sheet 2/22; FIGS. 3-6, respectively on Sheets 5-8/22; FIG. 16a, Sheet 18/22; and FIG. 20, Sheet 22/22]

Figure 7:
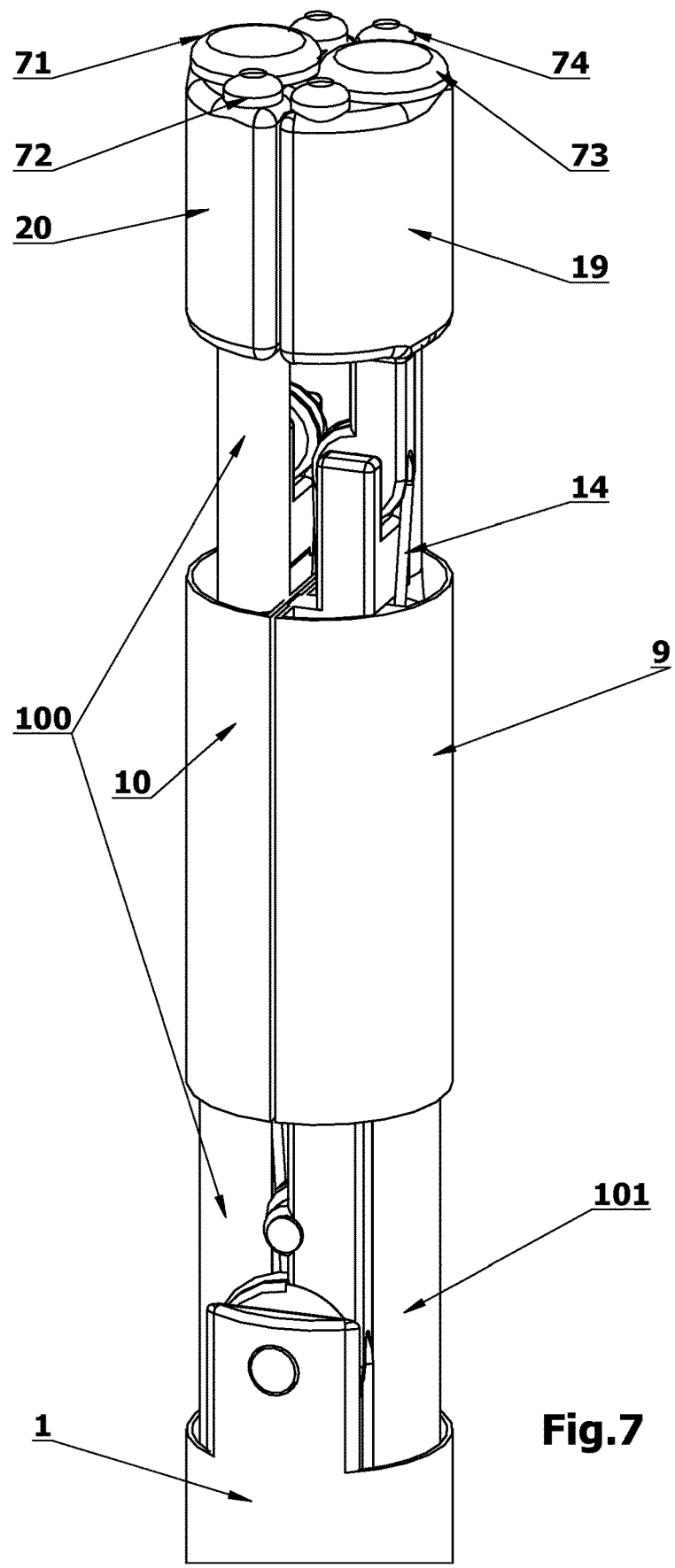
FIG. 7 is a view of the most preferred embodiment of the present invention similar in content to that shown in FIG. 6, but rotated 90-degrees from the illustration in FIG. 6 for a more detailed view of wiring, or conduit housing wiring, used to transmit electricity and data from/to a part of the imaging probes and/or a light source, which may also encase tubing that transmits fluids for irrigation purposes.

14. First cable/belt for transmitting convergence movement to first imaging probe (#19) [see FIG. 2a, Sheet 2/22; FIGS. 3-4, respectively on Sheets 5-6/22; FIGS. 6-7, Sheets 8-9/22; FIG. 16a, Sheet 18/22; and FIG. 20, Sheet 22/22]

15. Path guide pulley for first cable/belt (#14) [see FIG. 2a, Sheet 2/22; FIGS. 3-5, respectively on Sheets 5-7/22; and FIG. 20, Sheet 22/22]

16. Pin for mounting path guide pulley (#15) to a hinge on first probe arm (#9), which is similar in positioning and function to the hinge (#29) identified in FIG. 2a for second probe arm (#10) [see FIG. 2a, Sheet 2/22; and FIG. 3, Sheet 5/22]

17. Path guide pulley for second cable/belt (#13) [see FIG. 2a, Sheet 2/22 FIGS. 3-5, respectively on Sheets 5-7/22; and FIG. 20, Sheet 22/22]

18. Pin for mounting path guide pulley (#17) to hinge (#29) on second probe arm (#10) [see FIG. 2a, Sheet 2/22; FIGS. 3-4, respectively on Sheets 5-6/22; and FIG. 20, Sheet 22/22]

19. First imaging probe (also may be referred to as first diagnostic/sensor probe), in the alternative this also can be referred to as first therapeutic probe (may include all or part of the following in any combination: medical systems, non-medical systems, diagnostic systems, therapeutic systems, mechanical systems, camera systems, optical systems, light sources, different light wavelengths sensors, and different light wavelengths transmitters, fiber-optic systems, light emitting diode (LED) systems, fluorescence imaging systems, ultrasound systems, magnetic resonance imaging (MRI) systems, radiation systems, radio-frequency systems, laser systems, devices using electrical power to function, devices using non-electrical forms of energy to function, distance sensors, position sensors, cautery systems, irrigation systems, anti-fogging materials, anti-smudging materials, fluid-repellant materials, scissors, graspers, clamps, and forceps) [see FIG. 1, Sheet 1/22; FIG. 2a, Sheet 2/22; FIGS. 3-5, respectively on Sheets 5-7/22; FIG. 7, Sheet 9/22; FIG. 10, Sheet 12/22; FIG. 16a, Sheet 18/22; FIGS. 17a and 17b, Sheet 19/22; and FIGS. 19-20, Sheets 21-22/22]

20. Second imaging probe (also may be referred to as second diagnostic/sensor probe), in the alternative this also can be referred to as second therapeutic probe (may include all or part of the following in any combination: medical systems, non-medical systems, diagnostic systems, therapeutic systems, mechanical systems, camera systems, optical systems, light sources, different light wavelengths sensors, and different light wavelengths transmitters, fiber-optic systems, light emitting diode (LED) systems, fluorescence imaging systems, ultrasound systems, magnetic resonance imaging (MRI) systems, radiation systems, radio-frequency systems, laser systems, devices using electrical power to function, devices using non-electrical forms of energy to function, distance sensors, position sensors, cautery systems, irrigation systems, anti-fogging materials, anti-smudging materials, fluid-repellant materials, scissors, graspers, clamps, and forceps) [see FIG. 1, Sheet 1/22; FIG. 2a, Sheet 2/22; FIGS. 3-7, respectively on Sheets 5-9/22; FIG. 10, Sheet 12/22; FIG. 16a, Sheet 18/22; FIGS. 17a and 17b, Sheet 19/22; and FIGS. 19-20, Sheets 21-22/22]

21. Cable/belt housed in main tubular shaft (#1) and used with an extension (#51) between gearbox casing (#66) and dual groove pulley (#11) to transmit convergence movement to first imaging probe (#19) [see FIG. 2a, Sheet 2/22; FIG. 3, Sheet 5/22; FIG. 6, Sheet 8/22; and FIG. 16a, Sheet 18/22]

22. Cable/belt housed in main tubular shaft (#1) and used with an extension (#51) between gearbox casing (#66) and dual groove pulley (#12) to transmit convergence movement to second imaging probe (#20) [see FIG. 2a, Sheet 2/22; FIG. 3, Sheet 5/22; FIG. 6, Sheet 8/22; and FIG. 16a, Sheet 18/22]

23. Cable/belt housed in main tubular shaft (#1) and used with extension (#52) between gearbox casing (#66) and dual groove pulley (#11) for opening and closing of first probe arm (#9) [see FIG. 2a, Sheet 2/22; FIG. 3, Sheet 5/22; FIG. 6, Sheet 8/22; and FIG. 17a, Sheet 19/22]

24. Cable/belt housed in main tubular shaft (#1) and used with extension (#53) between gearbox casing (#66) and dual groove pulley (#12) for opening and closing of second probe arm (#10) [see FIG. 2a, Sheet 2/22; FIG. 3, Sheet 5/22; FIG. 6, Sheet 8/22; and FIG. 17a, Sheet 19/22]

25. Opening in the proximal end of one of the two longitudinal channels (#2) on main tubular shaft (#1) allowing entry into main tubular shaft (#1) of slider cable/belt (#8) [see FIG. 2a, Sheet 2/22]

26. Set of two path guide pulleys positioned within the proximal end of the main tubular shaft (#1) near the opening (#25), one of its pulleys used with slider cable/belt (#8) and the other of its pulleys used with extensions part 1 and 2 (#44, #45) of slider cable/belt (#8) [see FIG. 2a, Sheet 2/22; FIG. 11, Sheet 13/22; and FIG. 12a, Sheet 14/22]

27. Spring between convergence adjust button with rod (#59) and the convergence mechanism core rod (#57) [see FIG. 2b, Sheet 3/22; and FIG. 9 Sheet, 11/22; also unmarked in FIGS. 13a-14c and 15c, respectively on Sheets 15/22, 16/22, and 17/22]

28. Cable crimp sleeve to fix cables/belts (#13, #14, #21, #22) respectively to the corresponding dual groove pulley (#11 or #12) [see FIG. 2a, Sheet 2/22; FIG. 3, Sheet 5/22; and FIGS. 16c and 16d, Sheet 18/22]

29. Hinge identified in probe arm (#10) for mounting path guide pulley (#17) with pin (#18) for use with first imaging probe cable/belt (#13) [see FIG. 2a, Sheet 2/22; and FIGS. 3-4, Sheets 5-6/22]

30. Dual groove pulley related to probe arms adjust button (#58) and used with cable/belt extensions (#52, #53) and cables/belts (#23, #24) for opening and closing of probe arms (#9, #10) [see FIG. 2b, Sheet 3/22; and FIG. 17a, Sheet 19/22]

31. Bottom teeth of convergence adjust button with rod (#59) which engage top teeth (#60) of convergence mechanism core rod (#57) [see FIG. 2b, Sheet 3/22; and FIG. 9, Sheet 11/22]

Figure 8:
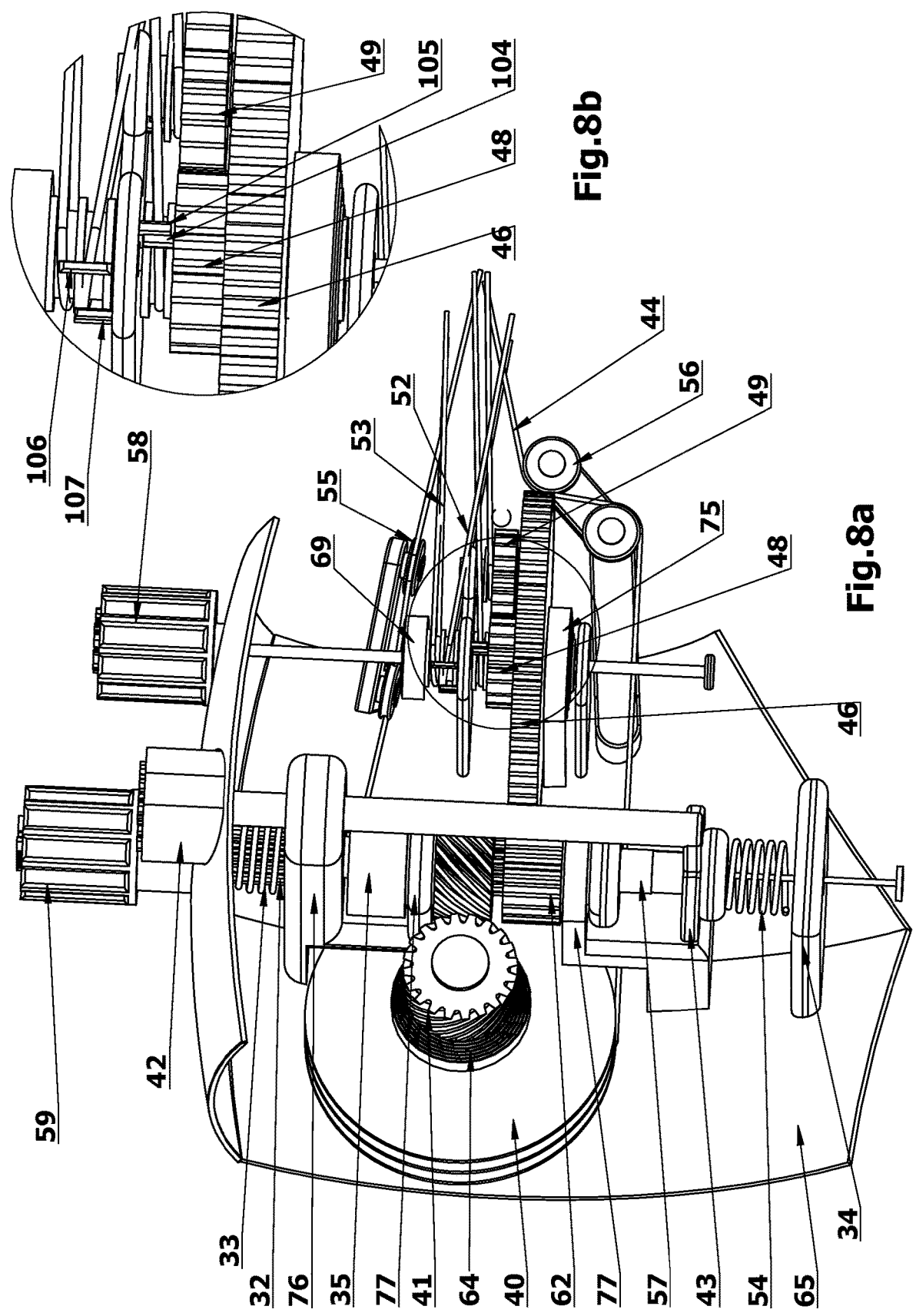
FIG. 8a is a sectioned view of a portion of the gearbox in the invention in FIG. 1, showing portions of the first, second, and third movement transmitting means that may be associated with the gearbox.
FIG. 8b is an enlarged view of a portion of the third movement transmitting means in FIG. 8a, which more clearly shows the configuration, positioning, and engagement of several pulley stops and gears.

32. Slider-related locking gear in the convergence mechanism combination, locks slider-related helical gear (#35) during manual convergence of imaging probes (#19, #20) initiated by Convergence adjust Button (#59) after the introduction of main tubular shaft (#1) into a cavity while choosing (converging on) a target object (#94) as in FIG. 15b, sheet 17/22 [see FIG. 2b, Sheet 3/22; FIGS. 8-9, Sheets 10-11/22; and FIGS. 13b, 14b, and 15b, respectively on Sheets 15-17/22]

33. Spring between slider-related locking gear (#32) and bushing/bracket with internal teeth (#76) [see FIG. 2b, Sheet 3/22; and FIGS. 8-9, Sheets 10-11/22; also unmarked in FIGS. 13a-14c, Sheets 15/22 and 16/22]

34. Bushing/Bracket (without teeth) fixed to gearbox backbone (#65) and used to mount the rod of convergence adjust button (#59), in alternative configurations it can also represent an electromagnet, a battery, energy storage device, energy producing device, and/or energy receiving device [see FIGS. 8-9, Sheets 10-11/22]

35. Slider-related helical gear with external teeth (#37) and internal teeth (#36) in the convergence mechanism combination, with its helical external teeth (#37) engaging the external teeth of helical gear (#41) [see FIG. 2b, Sheet 3/22; FIGS. 8-9, Sheets 10-11/22; and FIGS. 13b, 14b, and 15b, respectively on Sheets 15-17/22]

36. Internal teeth of slider-related helical gear (#35) which engage the external side teeth (#61) of the convergence mechanism core rod (#57) when it is simultaneously engaging Internal teeth (#38) of imaging probes convergence-related gear (#39) during convergence of imaging probes (#19, #20) using the slider (#6) (engaging first and second movement transmitting means) as see FIG. 14b, sheet 16/22 [see FIG. 2b, Sheet 3/22; FIG. 9, Sheet 11/22; and FIGS. 13c, 14c, and 15c, respectively on Sheets 15-17/22]

37. Helical external teeth of slider-related helical gear (#35) [see FIG. 2b, Sheet 3/22; and FIG. 9, Sheet 11/22]

38. Internal teeth of imaging probes convergence-related gear (#39) which engage the external side teeth (#61) of the convergence mechanism core rod (#57) during manual convergence of imaging probes (#19,20) using convergence adjust button (#59) as see FIG. 15b, sheet 17/22, and can also engage the external side teeth (#61) of the convergence mechanism core rod (#57) when it is simultaneously engaging internal teeth (#36) of slider related helical gear (#35) during convergence of imaging probes (#19,20) using the slider (#6) (engaging first and second movement transmitting means) as see FIG. 14b, sheet 16/22 [see FIG. 2b, Sheet 3/22; FIG. 9, Sheet 11/22; and FIGS. 13c, 14c, and 15c, respectively on Sheets 15-17/22]

39. Imaging probes convergence-related gear with external teeth (#62) and internal teeth (#38) in the convergence mechanism combination, with its external teeth (#62) engaging the external teeth of gear (#46) [see FIG. 2b, Sheet 3/22; FIG. 9, Sheet 11/22; and FIGS. 13b, 14b, and 15b, respectively on Sheets 15-17/22]

40. Large dual groove pulley with associated helical gear (#41) situated in gearbox casing (#66) and related to movement of slider (#6) via cable/belt (#8) and part 1 and 2 extensions (#44, #45) of slider cable/belt (#8) [see FIG. 2b, Sheet 3/22; FIG. 8, Sheet 10/22; and FIGS. 12a and 12b, Sheet 14/22]

41. Helical gear with external teeth associated with large dual groove pulley with helical gear (#40) [see FIG. 2b, Sheet 3/22; FIG. 8, Sheet 10/22; and FIG. 12b, Sheet 14/22]

42. Reset button with rod used to engage/disengage first and second movement transmitting means [see FIG. 1, Sheet 1/22; FIG. 2b, Sheet 3/22; and FIGS. 8-9, Sheets 10-11/22; and FIGS. 13b, 14b, and 15b, respectively on Sheets 15-17/22]

43. Ring at the distal end of reset button with rod (#42), engages the enlarged distal end of convergence mechanism core rod (#57) to compress spring (#54) against bushing/bracket (#34), releasing the connection between the external side teeth (#61) of the convergence mechanism core rod (#57) and the internal teeth (#36) of slider-related helical gear (#35) [see FIG. 2b, Sheet 3/22; FIGS. 8-9, Sheets 10-11/22; and FIGS. 13b, 14b, and 15b, respectively on Sheets 15-17/22]

44. Extension part 1 of slider cable/belt (#8) situated in gearbox casing (#66), associated with set of two path guide pulleys (#56) and extending between the set of two path guide pulleys (#26) and the large dual groove pulley with helical gear (#40) [see FIG. 2b, Sheet 3/22; FIG. 8, Sheet 10/22; and FIGS. 12a and 12b, Sheet 14/22]

45. Extension part 2 of slider cable/belt (#8) situated in gearbox casing (#66), associated with set of two path guide pulleys (#55) and extending between the set of two path guide pulleys (#26) and the large dual groove pulley with helical gear (#40) [see FIG. 2b, Sheet 3/22; FIG. 8, Sheet 10/22; and FIGS. 12a and 12b, Sheet 14/22]

46. Dual gear with pulley related to imaging probes convergence (the smaller diameter gear is separately identified by the number 48, and its pulley is separately identified by the number 78) [see FIG. 2b, Sheet 3/22; FIG. 8, Sheet 10/22; and FIG. 16b, Sheet 18/22]

47. Flat coiled spring for dual gear with pulley (#46) [see FIG. 2b, Sheet 3/22]

48. Small diameter gear with pulley in dual gear with pulley (:/146) [see FIG. 2b, Sheet 3/22; FIG. 8, Sheet 10/22; and FIG. 16b, Sheet 18/22]

49. Gear with pulley related to imaging probes convergence (its pulley is separately identified by the number 79) [see FIG. 2b, Sheet 3/22; FIG. 8, Sheet 10/22; and FIG. 16b, Sheet 18/22]

50. Pin for mounting gear with pulley (#49) in working engagement with small diameter gear with pulley (#48) [see FIG. 2b, Sheet 3/2]

51. Extensions of cables/belts (#21, #22) located in gearbox casing (#66) which are used for imaging probe (#19, #20) convergence and relate to the pulleys (#79, #78) respectively associated with gear with pulley (#49) and dual gear with pulley (#46), which includes the smaller diameter gear (#48) [see FIG. 2b, Sheet 3/22; and FIGS. 16a and 16b, Sheet 18/22]

52. Cable/belt located in gearbox (#66) and related to dual groove pulley (#30) which provides extension of the cable/ belt (#23) connected to the pulley-like structure (#102) on the proximal end of first probe arm (#9) and used concurrently with cable/belt (#53) for opening and closing of probe arms (#9, #10) [see FIG. 2b, Sheet 3/22; FIG. 8, Sheet 10/22; and FIG. 17a, Sheet 19/22]

53. Cable/belt located in gearbox (#66) and related to dual groove pulley (#30) which is an extension of the cable/belt (#24) connected to the pulley-like structure (#102) on the proximal end of second probe arm (#10) and used concurrently with cable/belt (#52) for opening and closing of probe arms (#9, #10) [see FIG. 2b, Sheet 3/22; FIG. 8, Sheet 10/22; and FIG. 17a, Sheet 19/22]

54. Spring between the enlarged distal end of convergence mechanism core rod (#57) and the bushing/bracket (#34) secured to gearbox backbone (#65) [see FIG. 2b, Sheet 3/22; FIGS. 8-9, Sheets 10-11/2; and FIGS. 13b, 14b, and 15b, respectively on Sheets 15-17/22]

55. Set of two path guide pulleys housed within gearbox casing (#66) and used with extension part 2 (#45) of slider cable/belt (#8) and the large dual groove pulley (#40) with associated helical gear (#41) [see FIG. 8, Sheet 10/22; and FIG. 12a, Sheet 14/22]

56. Set of two path guide pulleys housed within gearbox casing (#66) and used with the extension part 1 (#44) of slider cable/belt (#8) and the large dual groove pulley (#40) with associated helical gear (#41) [see FIG. 8, Sheet 10/22; and FIG. 12a, Sheet 14/22]

57. Convergence mechanism core rod [see FIG. 2b, Sheet 3/22, FIGS. 8-9, Sheets 10-11/22; and FIGS. 13b, 14b, and 15b, respectively on Sheets 15/22, 16/22, and 17/22]

58. Probe arms adjust button for opening and closing of probe arms (#9, #10) [see FIG. 1, Sheet 1/22; FIG. 2b, Sheet 3/22; FIG. 8, Sheet 10/22; and FIG. 17a, Sheet 19/22]

59. Convergence adjust button with elongated rod for manual convergence of first and second imaging probes (#19, #20) during selection of a visual target (#94) [see FIG. 1, Sheet 1/22; FIG. 2b, Sheet 3/22; and FIGS. 8-9, Sheets 10-11/2; and FIGS. 13b, 13c, 14b, 14c, 15b, and 15c, respectively on Sheets 15-17/22]

60. External top teeth of the convergence mechanism core rod (#57) which engage bottom teeth (#31) on convergence adjust button (#59) [see FIG. 2b, Sheet 3/22; and FIG. 9, Sheet 11/22; and FIG. 15b, Sheet 17/22]

61. External side teeth of the convergence mechanism core rod (#57) that can engage internal teeth (#36 and #38) respectively on slider-related helical gear (#35) and imaging probes convergence-related gear (#39) [see FIG. 2b, Sheet 3/22; FIG. 9, Sheet 11/22; and FIGS. 13b, 14b, and 15b, respectively on Sheets 15-17/22]

62. External teeth of imaging probes convergence-related gear (#39) [see FIG. 2b, Sheet 3/22; and FIG. 8, Sheet 10/22]

63. First shelf on backbone (#65) of gearbox casing (#66) used to mount path guide pulleys (#55) for slider cable/belt part 2 (#45) [see FIG. 2c, Sheet 4/22]

64. Flat coiled spring associated with large dual groove pulley (#40) with helical gear (#41), and related to movement of slider (#6) [see FIG. 2c, Sheet 4/22; and FIG. 8, Sheet 10/22]

65. Backbone of gearbox casing (#66) [see FIG. 2c, Sheet 4/22; and FIG. 8, Sheet 10/22]

66. Gearbox casing [see FIG. 1, Sheet 1/22; and FIG. 2c, Sheet 4/22]

67. Handle depending from gearbox casing (#66) [see FIG. 1, Sheet 1/22; and FIG. 2c, Sheet 4/22]

68. Second shelf on gearbox backbone (#65) used to mount path guide pulleys (#56) for slider cable/belt part 1 (#44) [see FIG. 2c, Sheet 4/22]

69. Flat coiled spring for returning the probe arms adjust button (#58) used for opening and closing probe arms (#9, #10) to the neutral position, placing probe arms (#9, #10) in their closed position adjacent to one another [see FIG. 2c, Sheet 4/22; and FIG. 8, Sheet 10/22]

70. Rail assembly inside of slider (#6) engaging cable/belt (#8) and channels (#2) for support of slider (#6) on the external surface of main tubular shaft (#1), allowing slider (#6) to move smoothly back and forth guided by the two channels (#2), may also use rollers 99 for its engagement of channels 2 [see FIG. 3, Sheet 5/22; and FIG. 12c, Sheet 14/22]

71. Representation of a camera in the second imaging probe (#20), (may include all or part of the following in any combination: medical systems, non-medical systems, diagnostic systems, therapeutic systems, mechanical systems, camera systems, optical systems, light sources, different light wavelengths sensors, and different light wavelengths transmitters, fiber-optic systems, light emitting diode (LED) systems, fluorescence imaging systems, ultrasound systems, magnetic resonance imaging (MRI) systems, radiation systems, radiofrequency systems, laser systems, devices using electrical power to function, devices using non-electrical forms of energy to function, distance sensors, position sensors, cautery systems, irrigation systems, antifogging materials, anti-smudging materials, fluid-repellant materials, scissors, graspers, clamps, and forceps) [see FIG. 4, Sheet 6/22; and FIGS. 6-7, Sheets 8-9/22]

72. Light source which can be transmitted via fiber-optics or produced by light-emitting diodes (LED'S), (may also include all or part of the following in any combination: medical systems, non-medical systems, diagnostic systems, therapeutic systems, mechanical systems, camera systems, optical systems, light sources, different light wavelengths sensors, and different light wavelengths transmitters, fiber-optic systems, light emitting diode (LED) systems, fluorescence imaging systems, ultrasound systems, magnetic resonance imaging (MRI) systems, radiation systems, radio-frequency systems, laser systems, devices using electrical power to function, devices using non-electrical forms of energy to function, distance sensors, position sensors, cautery systems, irrigation systems, anti-fogging materials, anti-smudging materials, fluid-repellant materials, scissors, graspers, clamps, and forceps) [see FIG. 4, Sheet 6/22; FIGS. 6-7, Sheets 8-9/22; and FIG. 20, Sheet 22/22]

73. Representation of a camera in the first imaging probe (#19), (may include all or part of the following in any combination: medical systems, non-medical systems, diagnostic systems, therapeutic systems, mechanical systems, camera systems, optical systems, light sources, different light wavelengths sensors, and different light wavelengths transmitters, fiber-optic systems, light emitting diode (LED) systems, fluorescence imaging systems, ultrasound systems, magnetic resonance imaging (MRI) systems, radiation systems, radio-frequency systems, laser systems, devices using electrical power to function, devices using non-electrical forms of energy to function, distance sensors, position sensors, cautery systems, irrigation systems, anti-fogging materials, anti-smudging materials, fluid-repellant materials, scissors, graspers, clamps, and forceps) [see FIGS. 6-7, Sheets 8-9/22]

74. Light source which can be transmitted via fiber-optics or produced by light-emitting diodes (LED'S), (may also include all or part of the following in any combination: medical systems, non-medical systems, diagnostic systems, therapeutic systems, mechanical systems, camera systems, optical systems, light sources, different light wavelengths sensors, and different light wavelengths transmitters, fiber-optic systems, light emitting diode (LED) systems, fluorescence imaging systems, ultrasound systems, magnetic resonance imaging (MRI) systems, radiation systems, radio-frequency systems, laser systems, devices using electrical power to function, devices using non-electrical forms of energy to function, distance sensors, position sensors, cautery systems, irrigation systems, anti-fogging materials, anti-smudging materials, fluid-repellant materials, scissors, graspers, clamps, and forceps) [see FIGS. 6-7, Sheets 8-9/22]

75. Flat coiled spring associated with dual gear with pulley (#46) for returning imaging probes (#19, #20) to neutral position [see FIG. 8, Sheet 10/22]

76. Bushing/Bracket with internal teeth fixed to gearbox backbone (#65), used to mount the convergence mechanism combination, including the slider-related locking gear (#32) while it assists in stopping slider-related helical gear (#35) during manual convergence of imaging probes (#19, #20) initiated by convergence adjust button (#59) [see FIG. 9, Sheet 11/22; and FIGS. 13c, 14c, and 15c, respectively on Sheets 15-17/22]

77. Bushings/Brackets fixed to gearbox backbone (#65) to mount gears (#35 and #39) of the convergence mechanism combination [see FIG. 9, Sheet 11/22; and FIGS. 13b, 14b, and 15b, respectively on Sheets 15-17/22]

78. Pulley of the small diameter gear with pulley (#48), which is part of the dual gear with pulley (#46) and related to imaging probes convergence [see FIG. 16b, Sheet 18/22]

79. Pulley of the gear with pulley (#49) related to imaging probes convergence [see FIG. 16b, Sheet 18/22]

80. Hinge at the distal end of first probe arm (#9) providing moving connection of first imaging probe (#19) [see FIG. 17c, Sheet 19/22]

81. First dual groove pulley engaged to second dual groove pulley (#84) with 2 sets of cables (first cable (#82) and second cable (#83)) where the end attachment of each (#85 and #86) is fixed to the independent winding groove it relates to and rolled in the opposite direction from the other cable (#85 or #86) in the related independent winding groove, this configuration providing a sturdy, non-slipping pulley cable system which is shown in part in large dual groove pulley (#40) and can be used to replace other pulleys or gears in the present invention endoscope 93 [see FIG. 18a, Sheet 20/22]

82. First cable/belt/wire engaged to first and second dual groove pulley (#81 and 84) this configuration provide sturdy, non-slipping pulley cable system which is shown in part in large dual groove pulley (#40) and can be used to replace other pulleys or gears in the present invention endoscope 93 [see FIG. 18a, Sheet 20/22]

83. Second cable/belt/wire engaged to first and second dual groove pulley (#81 and 84) this configuration provide sturdy non-slip pulley cable system which is shown in part in large dual groove pulley (#40) and can be used in other pulleys in the present invention [see FIG. 18a, Sheet 20/22]

84. Second dual groove pulley engaged to first dual groove pulley (#81) with 2 sets of cables (first cable (#82) and second cable (#83)) where the end attachment of each (#85 and 86) is fixed to the independent winding groove it relates to and rolled in the opposite direction from the other cable (#85 or #86) in the related independent winding groove, this configuration providing a sturdy, non-slipping pulley cable system which is shown in part in large dual groove pulley (#40) and can be used to replace other pulleys or gears in the present invention endoscope 93 [see FIG. 18a, Sheet 20/22]

85. Cable/belt/wire end attachment point on first dual groove pulley (#81), with a set of two on each pulley in a configuration that provides sturdy, non-slipping pulley cable system which is shown in part in large dual groove pulley (#40) and can be used to replace other pulleys or gears in the present invention endoscope 93 [see FIG. 18a, Sheet 20/22]

86. Cable/belt/wire end attachment point on second dual groove pulley (#84), with a set of two on each pulley in a configuration that provides sturdy, non-slipping pulley cable system which is shown in part in large dual groove pulley (#40) and can be used to replace other pulleys in the present invention [see FIG. 18a, Sheet 20/22]

87. Aperture leading to optional channel (not shown) used for the insertion of an independent instrument (not shown) needed to manipulate the target object (#94) during use of the present invention [see FIG. 1, Sheet 1/22]

88. Unit that can be used as a laser pointer, an endoscope-to-target distance sensor, or both, and/or may include all or part of the following in any combination: medical systems, non-medical systems, diagnostic systems, therapeutic systems, mechanical systems, camera systems, optical systems, light sources, different light wavelengths sensors, and different light wavelengths transmitters, fiber-optic systems, light emitting diode (LED) systems, fluorescence imaging systems, ultrasound systems, magnetic resonance imaging (MRI) systems, radiation systems, radio-frequency systems, laser systems, devices using electrical power to function, devices using non-electrical forms of energy to function, distance sensors, position sensors, cautery systems, irrigation systems, anti-fogging materials, anti-smudging materials, fluid-repellant materials, scissors, graspers, clamps, and forceps) [see FIG. 19, Sheet 21/22; and FIG. 20, Sheet 22/22]

89. Not-to-scale representation of visual display system [see FIG. 19, Sheet 21/22]

90. Not-to-scale representation of robotic systems [see FIG. 19, Sheet 21/22]

91. Not-to-scale representation of electric motor for automated convergence adjustment and 3-D endoscope functions control and in integration with robotic systems (#90) [see FIG. 19, Sheet 21/22]

92. Not-to-scale representation of computer component for automated convergence adjustment and 3-D endoscope functions control and in integration with robotic systems (#90) [see FIG. 19, Sheet 21/22]

93. Not-to-scale representation of the present invention 3-D endoscope [see FIG. 19, Sheet 21/22]

94. Not-to-scale representation of a visual target [see FIG. 19, Sheet 21/22]

95. Not-to-scale representation of robotic systems arms, tools and connections [see FIG. 19, Sheet 21/22]

96. Not-to-scale representation of wireless receiver/transmitter related to 3-D endoscope (#93) [see FIG. 19, Sheet 21/22]

97. Not-to-scale representation of wireless receiver/transmitter related to visual display system (#89) [see FIG. 19, Sheet 21/22]

98. Not-to-scale representation of wireless receiver/transmitter related to robotic systems (#90) [see FIG. 19, Sheet 21/22]

99. Roller related to movement of slider (#6) guided by channels (#2) [see FIG. 12d, Sheet 14/22]

100. Wire for second imaging probe (#20) to transmit electricity and data from/to a part of second imaging probe (#71) and light source (#72) (may encase tubing that transmit fluids for irrigation) [see FIG. 7, Sheet 9/22]

101. Wire for first imaging probe (#19) to transmit electricity and data from/to a part of first imaging probe (#73) and light source (#74) (may encase tubing that transmit fluids for irrigation) [see FIG. 7, Sheet 9/22]

102. Two pulley-like structures each depending from the proximal end of a different one of the two probe arms (#9, #10) [see FIG. 3, Sheet 5/22; and FIGS. 17b and 17c, Sheet 19/22]

103. Two pulley-like structures each depending from the proximal end of a different one of the two imaging probes (#19, #20) [see FIG. 3, Sheet 5/22]

104. Pulley stop for imaging probe pulley (#78) [see FIG. 2b, Sheet 3/22, FIG. 8b, Sheet 10/22, and FIG. 16b, Sheet 18/22]

105. Pulley opposing stop for imaging probe pulley (#78) attached to bracket/shelf (#108) [see FIG. 2c, Sheet 4/22 and FIG. 8b, Sheet 10/22]

106. Pulley stop for for imaging probe pulley (#79) [FIG. 8b, Sheet 10/22]

107. Pulley opposing stop for imaging probe pulley (#79) attached to bracket/shelf (#108) [see FIG. 2c, Sheet 4/22 and FIG. 8b, Sheet 10/22]

108. Bracket/shelf carrying rod for probe arms adjust button (#58) that works as an axle for dual groove pulley (#30) and pulley (#78) with its connected gear (#48/#46) [see FIG. 2c, Sheet 4/22]

Before structure in the most preferred embodiment of the present invention 3-D endoscope 93 is described using the accompanying FIGS. 1-20 on drawing sheets 1-22, an example of a preferred method of use for the most preferred embodiment of the present invention endoscope 93 in a medical application will be described below for achieving 3-dimensional human vision simulated imaging with real dynamic convergence for a visual target 94 situated within a body cavity (not shown). It must be understood that the same steps, the same step sequence, and the same components identified in medical applications may also be applicable to many uses of the present invention 3-D endoscope 93 in search/rescue, scientific research, investigative, and other non-medical applications where 3-dimensional human vision simulated imaging with real dynamic convergence can assist in the observation/identification or other interaction with a visual target 94 accessible through a small or narrow opening in a wall or other access-restrictive barrier. It should also be appreciated that the disclosure herein of the present invention 3-D endoscope 93 and its methods of use only provide examples of selected embodiments and methods to enable one of ordinary skill to make and use its best modes, and many other variations, combinations, and equivalents also exist which are not specifically mentioned. The present invention should therefore not be considered as limited to the embodiments, methods, and examples specifically provided herein, but instead encompassing all embodiments and methods within the scope and spirit of the invention as disclosed and defined in the accompanying claims. Three movement transmitting means and one control means define the use of present invention 3-D endoscope 93 presented below, while it employs imaging probes 19 and 20 to achieve 3-dimensional human vision simulated imaging with real dynamic convergence for viewing a selected visual target 94, both manually via convergence adjustment button 59 while selecting a visual target 94, and as a consequence of the forward and backward movement of the slider 6 along main tubular shaft 1. In the paragraphs immediately following, preferred structure associated with each of the first, second, and third movement transmitting means will be described, each followed by a related paragraph entitled Mechanism of Action. In contrast, the control means will be subsequently described in the context of three specific modes (A-C) of engagement/disengagement of the first and second movement transmitting means relating to convergence/divergence of imaging probes 19 and 20.

First Movement Transmitting Means/Slider Mechanism—See FIG. 11 on Drawing Sheet 13/22 and FIGS. 12a-d on Drawing Sheet 14/22

It comprises the slider 6 that can move smoothly back and forth on the main tubular shaft 1, aided in its movement by the sliding rail assembly 70, and also preferably guided by the two channels 2 in the exterior surface of the main tubular shaft 1 and in other alternative configurations can include a combination rail and rollers 99, or only rollers 99. The slider 6 is connected to a cable 8 (and its continuing extensions 44 and 45) that extend between pulley 7 and a combined large dual groove pulley 40 and helical gear 41 that are located in the present invention gearbox casing 66, with cable 8 and its extensions 44 and 45 guided by several sets of path guide pulleys, preferably as follows: one set of two pulleys 26 located close to the proximal end of the main tubular shaft and two additional sets (55 and 56) of two pulleys each, that are located within the gearbox casing 66.

Mechanism of Action

When the main tubular shaft 1 of the present invention 3-D endoscope 93 is introduced inside an abdominal cavity (not shown), it goes through the access port in a cavity wall (not shown) without difficulty, but slider 6 does not pass through the access port because of its larger diameter. Should the 3-D endoscope 93 move forward inside the cavity toward a visual target 94, the forward movement makes the slider 6 move backward on the main tubular shaft 1. This movement of slider 6 is transmitted into the combined large dual groove pulley 40 with helical gear 41 in the gearbox casing 66 by the cable 8 and its continuing extensions (44 and 45), the movement of slider 6 making the combined large dual groove pulley 40 with helical gear 41 turn into one direction and cause a predetermined reduction in the slider 6 movement when transmitted by the smaller helical gear 41 associated with large dual groove pulley 40 to the external helical teeth 37 of the slider-related helical gear 35 of the control means/convergence mechanism combination (see FIGS. 8 and 9), which in turn can control its transmission to the second movement transmitting means/ imaging probes convergence mechanism (see FIGS. 16a-d on Sheet 18/22) to achieve convergence when appropriate.

In the alternative, should the 3-D endoscope 93 move backward inside the cavity away from visual target 94, the backward movement makes slider 6 move forward on main tubular shaft 1. This movement of slider 6 is caused by the flat coiled spring 64 associated with the large dual groove pulley 40 with associated helical gear 41. This movement of slider 6 is transmitted into the combined large dual groove pulley 40 with helical gear 41 in gearbox casing 66 by cable 8 and its continuing extensions 44 and 45, the movement of slider 6 making the combined large dual groove pulley 40 with helical gear 41 turn into the direction opposite to the previous turning movement of the combined large dual groove pulley 40 with helical gear 41 that occurred as a consequence of the 3-D endoscope 93 moving forward inside the cavity toward a visual target 94. Movement of the large dual groove pulley 40 with helical gear 41 in that opposite direction after having a predetermined reduction going through the smaller helical gear 41 is transmitted to the external helical teeth 37 of the slider-related helical gear 35 of the control means/convergence mechanism combination (see FIGS. 8 and 9), and if the control means/convergence mechanism combination so allows, the predetermined reduction in slider 6 is further transmitted to the second movement transmitting means/imaging probes convergence mechanism (see FIGS. 16*a-d* on Sheet 18/22) to achieve divergence in imaging probes 19 and 20.

Second Movement Transmitting Means/Imaging Probes Convergence Mechanism—See FIGS. 16*a-d* on Drawing Sheet 18/22

It comprises the first and second imaging probes 19 and 20 that are respectively movably mounted at the distal ends of the two probe arms 9 and 10, which in turn are located at the distal end of main tubular shaft 1 and are each preferably mounted to move toward and away from one another approximately 90-degrees to establish an approximate 180-degree range of motion from a fully closed position when probe arms 9 and 10 are adjacent to one another. Pulley stops 104 and 106 and pulley opposing stops 105 and 107 associated with imaging probe pulleys 78 and 79 limit the motion of probe arms 9 and 10 to approximately 180-degrees. While pulley stops 104 and 106 are connected respectively to imaging probe pulleys 78 and 79, pulley opposing stops 105 and 107 are each connected to a bracket/shelf 108 secured to gearbox backbone 65. At their proximal ends, first and second imaging probes 19 and 20 each have an associated pulley-like structure 103 (see FIG. 3) that are respectively connected by cables 14 and 13 to the dual groove pulleys 11 and 12 mounted at the distal end of main tubular shaft 1. The dual groove pulleys 11 and 12 are respectively connected through cables 21 and 22 in the main tubular shaft 1, in combination with their continuation cables 51 in the present invention gearbox casing 66, that extend respectively to the pulley part 78 of the smaller dual gear 48 (part of a large/small gear combination with pulley 46) and are also connected to the pulley part 79 of the gear with pulley 49 that moves in the opposite direction to smaller dual gear 48. The cables 13, 14, 21, and 22 are preferably attached firmly to pulleys 11 and 12 by cable crimp sleeves 28. In addition, cables 13 and 14 are guided into a path inside the two probe arms 9 and 10 respectively by the path guide pulleys 15 and 17 that are mounted on pins 18 and hinges 29 located near to the pulley-like structures 102 close to the proximal ends of probe arms 9 and 10.

Mechanism of Action

If the control means/convergence mechanism combination (see FIGS. 8 and 9) allows engagement of the first and second movement transmitting means, the reduced movement derived from slider 6 and created by the first movement transmitting means is then transmitted to the second movement transmitting means/imaging probes convergence mechanism. First, this movement is again reduced going through the connection of the external teeth 62 of the imaging probes convergence-related gear 39 (relatively smaller gear) with the external teeth of the relatively larger diameter gear of the dual gear with pulley 46 which transmits the reduced movement to its associated smaller gear 48 with pulley 78 that turns in the same direction as its associated large diameter gear 46, with this same movement being transmitted in an opposite direction to the gear 49 with pulley 79 having external teeth in working engagement with the external teeth of the smaller gear 48 with pulley 78. The resulting movement of gears 48 and 49 is transmitted through their respective pulleys 78 and 79, and their respectively connected cables 21 and 22, including the continuing extensions 51 thereof (in the present invention gearbox casing 66) to pulleys 11 and 12, and then respectively via cables 14 and 13 to the first and second imaging probes 19 and 20 to cause them to converge or diverge according to the direction of movement received from the first movement transmitting means/slider mechanism. When no force is exerted on the dual gear with pulley 46, as when the control means/convergence mechanism combination disengages the first and second movement transmitting means, the stored energy in the flat coiled spring 75 related to the dual gear with pulley 46 causes the large gear 46 to turn in the opposite direction to a predetermined position, returning the imaging probes 19 and 20 to a neutral position (no convergence) where they are oriented parallel to one another.

Third Movement Transmitting Means/Probe Arms Opening and Closing Mechanism—See FIGS. 17*a-c* on Drawing Sheet 19/22

It consists of the two probe arms 9 and 10 which are movably mounted at the distal end of the main tubular shaft 1, with the first and second imaging probes 19 and 20 movably mounted respectively to the distal end of the two probe arms 9 and 10. Each probe arm 9 and 10 has an associated pulley-like structure 102 (see FIG. 3) at its proximal end, with the pulley-like structures 102 connected by two cables 23 and 24 in the main tubular shaft 1, along with their respective continuation/extension cables 52 and 53 within the present invention gearbox casing 66, to the dual groove pulley 30 mounted on the elongated rod of the probe arms adjust button 58.

Mechanism of Action

Turning the probe arms adjust button 58 causes the dual groove pulley 30 mounted on the rod of probe arms adjust button 58 to turn in the same direction as the rod. This movement of dual groove pulley 30 is transmitted through the cables 52 and 53 in gearbox casing 66, along with their respective continuation cables 23 and 24 within main tubular shaft 1, to both of the probe arms 9 and 10, causing them to turn (close or open). The cable 53 in gearbox casing 66 is configured in the shape of a figure eight, which causes the one probe arm 10 connected to it to move in the opposite direction to the other probe arm 9, so that when the probe arms adjust button 58 is turned in one direction, it causes the probe arms 9 and 10 to close, while turning the probe arms adjust button 58 in the other direction causes probe arms 9 and 10 to open to the specific required distance allowing a user to control the inter-axial distance between the first and second imaging probes 19 and 20 respectively mounted on probe arms 9 and 10.

Figures 14A, 14B, 14C:
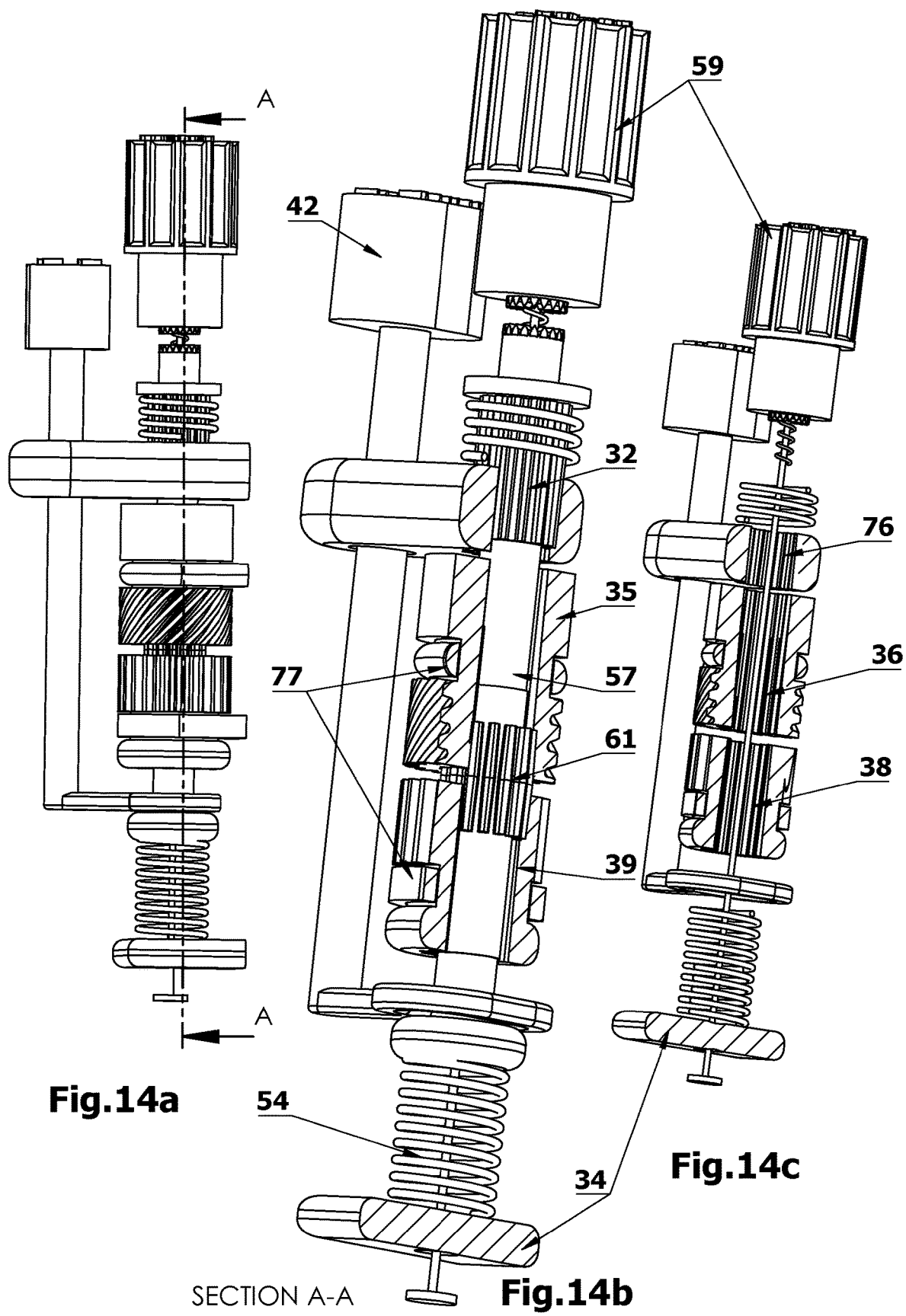

Control Means/Engaging-Disengaging the First and Second Movement Transmitting Means and Manual Convergence Means (Allowing a Visual Target 94 to be Selected)/Convergence Mechanism Combination—See FIG. 9 on Drawing Sheet 11/22, FIGS. 13*a-c* on Drawing Sheet 15/22, FIGS. 14*a-c* on Drawing Sheet 16/22, and FIGS. 15*a-c* on Drawing Sheet 17/22

The control means/convergence mechanism combination receives movement from either the slider 6 being transmitted through the first movement transmitting means to slider-related helical gear 35 of the control means/convergence mechanism combination, or from manual convergence adjust button with rod 59. The control means then controls whether the transmission of either movement is to be passed to, or not passed into, the second movement transmission means through its imaging probe convergence-related gear 39 to the first and second imaging probes 19 and 20 for convergence, divergence (being automatic and caused by the slider 6, or manual and caused by manual convergence adjust button 59, or does not move during the introduction of the present invention 3-D endoscope 93 to/from an access port in a cavity wall). The control means/convergence mechanism combination is usually present in one of three modes, represented in FIGS. 13*a-c*, 14*a-c*, and 15*a-c* respectively on drawing sheets 15/22, 16/22, and 17/22, as discussed in the following paragraphs under the titles of First Mode A, Second Mode B, and Third Mode C.

First Mode A—Disengaging First and Second Movement Transmitting Means/Fourth Movement Transmitting Means (Pushing Reset Button)—See FIGS. 13*a-c* on Drawing Sheet 15/22

During the introduction of the 3-D endoscope 93 into the abdominal cavity, the slider 6 should be able to move freely without causing convergence until: 1) it reaches its ZERO point with both probe arms 9 and 10 completely inside the abdominal cavity and clear of the abdominal wall (which can differ in thickness from one person to the other), and also clear of the access port/trocar and sleeve (which can differ in length from one brand to the other, and from one model to the other in the same brand); and 2) the probe arms 9 and 10 are opened and the distance between the first and second imaging probes (19, 20) is wide enough that the 3-D endoscope 93 movement toward the visual target 94 requires convergence. To allow slider 6 to move freely without causing convergence, the first and second movement transmitting means first have to be disengaged.

Mechanism of Action

Pushing the reset button 42 down causes the convergence mechanism core rod 57 to move down, allowing the external side teeth 61 on convergence mechanism core rod 57 to only be in contact with the internal teeth 38 of the imaging probes convergence-related gear 39 and clear internal teeth 36 of the slider-related helical gear 35, which allows the slider-related helical gear 35 to move independently from the imaging probes convergence-related gear 39, disengaging the first movement transmitting means from the second movement transmitting means. At that time, no force is exerted on the slider-related locking gear 32 except the spring 33 forces, causing it to be pushed up away from the bushing/brackets with internal teeth 76 fixed to gearbox backbone 65 so that the external teeth of the slider-related locking gear 32 are only in contact with the internal teeth of the bushing/brackets with internal teeth 76 fixed to gearbox backbone 65 and clear from the internal teeth 36 of slider related helical gear 35. That allows slider-related helical gear 35 to move freely and not to be locked in place with the bushing/brackets with internal teeth 76 fixed to gearbox backbone 65.

Second Mode B—Manual Convergence/Choosing a Visual Target (Pushing and Turning Convergence Adjust Button)—See FIGS. 15*a-c*

After the introduction of the 3-D endoscope 93 into the abdominal cavity, with both probe arms 9 and 10 completely inside the abdomen and opened by the third movement transmitting means, the slider 6 is now at its ZERO point. At this time choosing a visual target 94 is done using the manual convergence/control means which fixes first movement transmitting means/slider mechanism in place and allows the user to choose a visual target 94 manually by making the first and second imaging probes 19 and 20 converge initially on that visual target 94.

Mechanism of Action

Pushing the convergence adjust button 59 down causes the convergence mechanism core rod 57 to move down, making its external side teeth 61 only engaged with internal teeth 38 of imaging probes convergence-related gear 39 and remain clear of the internal teeth 36 of slider-related helical gear 35, allowing independent movement of the slider-related helical gear 35 from the imaging probes convergence-related gear 39 for disengagement of the first and second movement transmitting means. The convergence adjust button 59 also pushes the slider-related locking gear 32 down, causing it to move through the bushing/brackets with internal teeth 76 fixed to gearbox backbone 65, so that the external teeth of the slider-related locking gear 32 simultaneously contact the internal teeth of the bushing/brackets with internal teeth 76 fixed to gearbox backbone 65 and the internal teeth 36 of slider-related helical gear 35, that causes slider-related helical gear 35 to stop moving and to be locked in place with the bushing/bracket with internal teeth 76 fixed to gearbox backbone 65. At the same time the convergence adjust button 59 is pushed down, its bottom teeth 31 are placed in contact with external top teeth 60 of the convergence mechanism core rod 57 which engage rod 57 and button 59 together, so turning of the convergence adjust button 59 causes the convergence mechanism core rod 57 to turn simultaneously with it. In addition, because the external side teeth 61 of the convergence mechanism core rod 57 is concurrently in contact only with the internal teeth 38 of imaging probes convergence-related gear 39, turning of the convergence adjust button 59 only causes turning of the imaging probes convergence-related gear 39 which eventually causes the first and second imaging probes (19, 20) to converge on the chosen visual target 94.

Third Mode C—Engaging First and Second Movement Transmitting Means (Releasing Reset Button)—See FIGS. 14*a-c*

After the introduction of the 3-D endoscope 93 into the abdominal cavity, while both probe arms 9 and 10 are completely inside the abdomen and opened, the slider 6 is now at its ZERO point. At which time choosing a visual target 94 is done using the manual convergence/control means C (FIGS. 15*a-c*), after which the first and second movement transmitting means should be engaged, so that any movement of the slider 6 is thereafter translated into a convergence or divergence movement of the first and second imaging probes (19, 20) according to the direction of that movement.

Mechanism of Action

Releasing the reset button 42 for upward movement allows the spring 54 to push the convergence mechanism core rod 57 in an upward direction, placing its external side teeth 61 simultaneously in contact with both the internal teeth 38 of the imaging probes convergence-related gear 39 and internal teeth 36 of slider-related helical gear 35, which forces the slider-related helical gear 35 to move together with imaging probes convergence-related gear 39, engaging the first movement transmitting means with the second movement transmitting means. At that time, no force is exerted on the slider-related locking gear 32 except the spring 33 forces, causing it to be pushed up away from the bushing/brackets with internal teeth 76, fixed to gearbox backbone 65, so that the external teeth of the slider-related locking gear 32 are only in contact with the internal teeth of the bushing/brackets with internal teeth 76 fixed to gearbox backbone 65 and clear from the internal teeth 36 of slider related helical gear 35. That allows slider-related helical gear 35 to move freely and not to be locked in place with the bushing/brackets with internal teeth 76 fixed to gearbox backbone 65.

Figure 1:
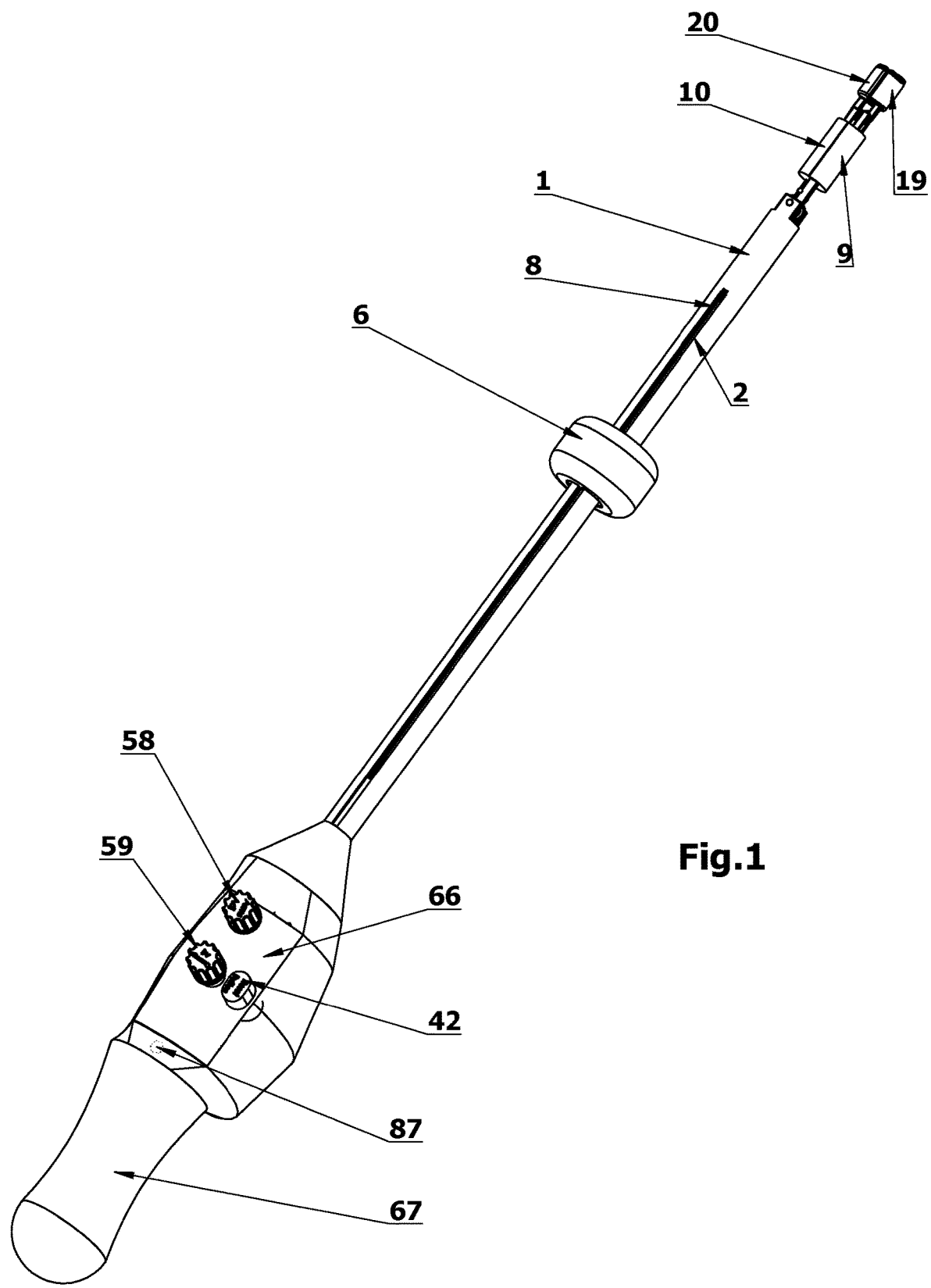
FIG. 1 illustrates a perspective view of the most preferred embodiment of the present invention.

FIGS. 1-7 show structural features in the most preferred embodiment of the present invention advanced endoscopic device 93 relating to slider 6 movement and the first and second movement transmitting means allowing the slider 6 movement to be used for achieving convergence/divergence in imaging probes (19, 20), or others of like kind. FIG. 1 shows the main tubular shaft 1 having a longitudinal channel 2 extending substantially along its length, and slider 6 associated with channel 2 for back-and-forth movement of slider 6 relative to the main tubular shaft 1. More than one channel 2 may be used, or in the alternative no channels 2 may be needed to assist slider 6 movement. Also in other configurations, depending upon the embodiment and application, channel 2 may represent a position sensor that helps to determine the position of the 3-D endoscopic device 93 in relation to its surroundings, with this positioning data used by a computer component to control convergence in like kind imaging probes (19, 20, or other). FIG. 1 also shows two side-by-side probe arms (9, 10) supported by the distal end of main tubular shaft 1, and the two imaging probes (19, 20) supported respectively by the distal ends of probe arms (9, 10). The configuration of the advanced present invention endoscope 93 illustrated in FIG. 1 is that typically selected for introduction of the main tubular shaft 1 through an opening or port (not shown) for viewing or otherwise interacting with a visual target 94 in a cavity. FIG. 1 further shows a gearbox casing 66 depending from the proximal end of main tubular shaft 1 and having an associated manual probe arm adjust button 58, a convergence adjust button with rod 57, and a reset button 42 all in close proximity to one another, which is preferred but not critical. The relative sizes, shapes, and locations of manual probe arm adjust button 58, convergence adjust button with rod 57, and reset button 42 are not limited to that shown in FIG. 1. An aperture 87 is also visible in FIG. 1 between gearbox casing 66 and a handle 67 depending from gearbox casing 66. It is intended for aperture 87 to lead to an optional channel (not shown) used for the insertion and concurrent use of at least one independent instrument (not shown) inside the cavity where the present invention is inserted. Independent instruments can include, but are not limited to, endoscopic scissors, graspers, and biopsy forceps. The relative length dimension of main tubular shaft 1 to that of gearbox casing 66 shown in FIG. 1 should not be considered as limiting. Also, the sizes and shapes of gearbox casing 66, handle 67, and slider 6 should not be considered as limiting to the structures depicted in FIG. 1. In addition, the number and location of handles 67 and apertures 87 used may be different in differing embodiments of the present invention endoscopic device 93, and one or more apertures 87 leading to one or more channels 2 can be used through gearbox casing 66 or elsewhere, including the main tubular shaft 1. Resetting imaging probes 19 and 20 to their neutral positioning (with no convergence, also referred to herein as zero convergence, where the longitudinal axes of imaging probes 19 and 20 are substantially parallel to one another) can be rapidly accomplished and is discussed above in the last sentence of paragraph [0059]. It would typically occur prior to entry of the present invention into a endoscopic port, prior to its withdrawal from a endoscopic port, may possibly be needed when redirecting imaging probes 19 and 20 to a new visual target 94, or otherwise as needed. If the reset sequence (mentioned above in paragraphs [0066], [0068], and [0076]) is not accomplished prior to entry of the present invention into a endoscopic port, imaging probes 19 and 20 may not be optimally positioned for successful entry into the endoscopic port. In addition, without the free movement of slider 6 through disengagement of the first and second movement transmitting means (see above paragraphs [0066] and [0068]), components of this invention could be placed at risk of breaking when laparoscopic entry is attempted.

FIG. 2a is an exploded view of some of the components in the first and second movement transmitting means of the most preferred embodiment of the present invention associated with main tubular shaft 1 and relating to slider 6 movement and the movement of imaging probes (19, 20) for their convergence/divergence. FIG. 2a shows slider 6 having a simple, sleek design, and the main tubular shaft 1 having a bore 5 through opposing sides of its distal end where a pin 4 is fixed to movably mount the proximal ends of the probe arms (9, 10) and the dual groove pulleys (11, 12) that respectively transmit convergence movement to the two imaging probes (19, 20) while supported by the distal ends of probe arms (9, 10). In addition, the belt 8 and guide path pulleys (7, 26) shown in FIG. 2a permit the back-and-forth movement of slider 6 longitudinally along main tubular shaft 1 via channel 2, channel opening 3, and channel opening 25. FIG. 2a also shows multiple belts/cables (13-14, 21-24) that are used with pulleys (11-12, 15, 17) to transmit slider 6 movement to gearbox casing 66, or reduced slider 6 movement from gearbox casing 66 to the imaging probes (19, 20) for their convergence/divergence. In contrast, FIG. 2b is an exploded view of some of the components in the first and second movement transmitting means that are housed in gearbox casing 66 and relate to the movement reduction occurring in gearbox casing 66. Many of these components are also shown in enlarged views in FIGS. 8a, 9, 12a, 13a-16b, and 17a. Via the belt/cable extensions (51, 52, 53, 55, 56), movement from slider 6 may be transmitted to gearbox casing 66 from some of the components shown in FIG. 2a (explained in more detail below), and if the control means (identified descriptively elsewhere herein) engages the first and second movement transmitting means, after its reduction the reduced slider 6 movement may be transmitted to imaging probes (19, 20) to affect their convergence or divergence.

Figure 2C:
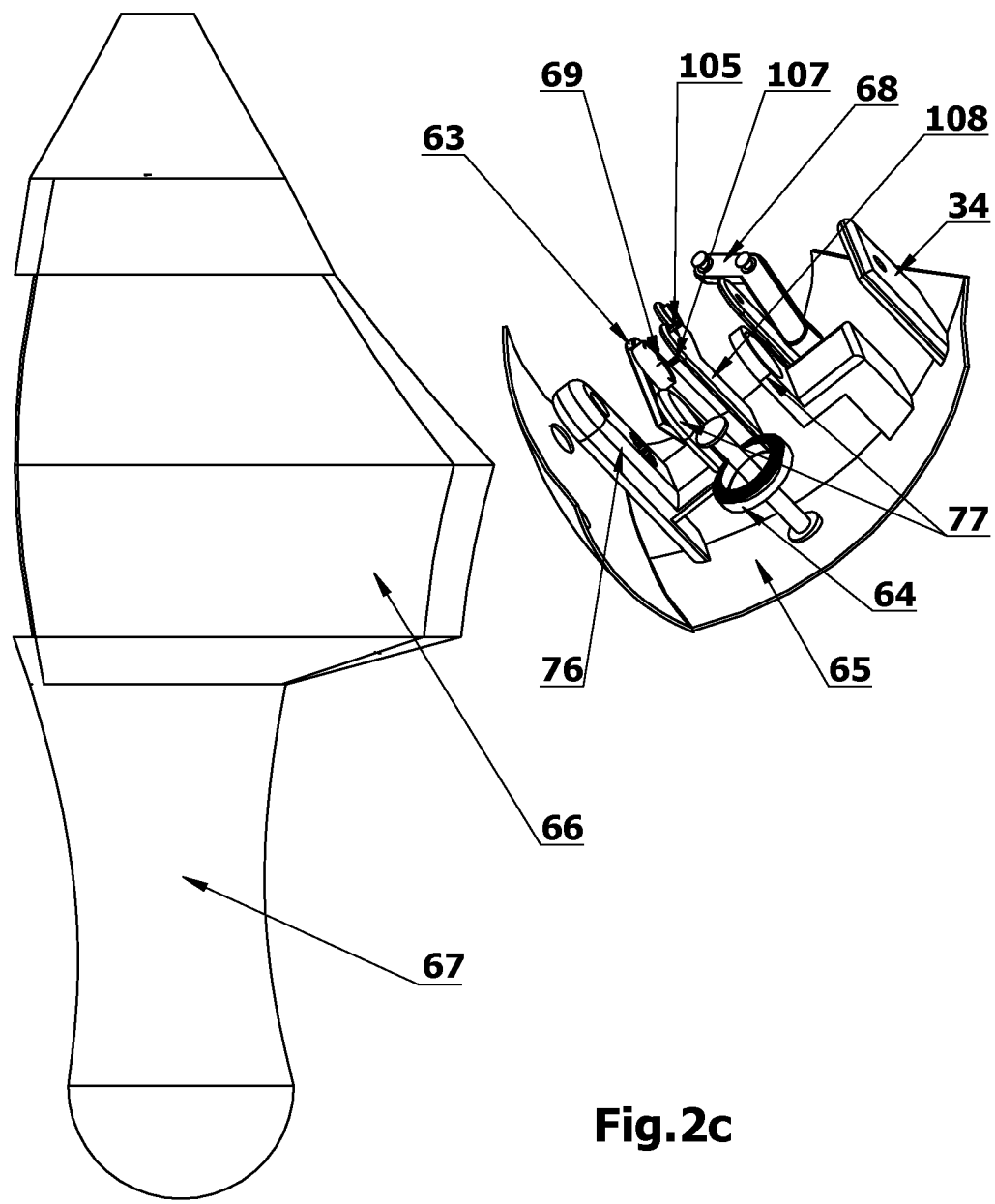
FIG. 2c includes side-by-side exterior and interior views of the gearbox in the invention shown in FIG. 1, with the interior view showing preferred bushings/brackets fixed to the gearbox backbone which are used for mounting and bracing portions of the control means that assist in controlling the engagement and disengagement of the first and second movement transmitting means.

FIG. 2c comprises external and interior views of the gearbox casing 66 in most preferred embodiment of the present invention, with the interior view on the right showing preferred bushings/brackets (76, 77, 34) and shelves (63, 68, 108) fixed to the gearbox backbone 65 which are used for mounting portions of the control means that assist in controlling the engagement and disengagement of the first and second movement transmitting means. FIG. 2c also shows a preferred flat coiled spring 69, the stored energy of which is used to return the probe arms adjust button 58 (employed for manual opening and closing of probe arms (9, 10) to the neutral position, placing probe arms (9, 10) in their closed position adjacent to one another. FIG. 2c also shows the pulley opposing stops 105 and 107 respectively used in association with the imaging probe pulleys 78 and 79 (see also FIGS. 8a and 16b) to prevent probe arms (9, 10) from moving through a combined distance of more than 180-degrees. In addition, in the external view of gearbox casing 66 on the left of FIG. 2c, handle 67 is also shown depending from gearbox casing 66. FIG. 3 is an enlarged view of the same components shown in the top portion of FIG. 2a. FIG. 4 is a perspective view from the side of the most preferred embodiment of the present invention, showing the movable connection between the probe arms (9, 10) and the distal end of the main tubular shaft 1, as well as the movable connection between each imaging probe (19, 20) and the probe arm (19, 20) supporting it. FIG. 4 also shows both imaging probes (19, 20) in a state of convergence. FIG. 5 is a transparent view of the most preferred embodiment of the present invention endoscope 93 that is similar in content to that shown in FIG. 4, with preferred placement of belts/cables and pulleys in the second movement transmitting means now shown. FIG. 6 is a perspective view of present invention endoscope 93 showing the connection of the probe arms (9, 10) to the distal end of the main tubular shaft 1, the connection of the imaging probes (19, 20) to the probe arms (9, 10), and the probe arms (9, 10) and imaging probes (19, 20) each in their closed positions. Dual groove pulleys 11 and 12 are visible in FIG. 6, as are cables/belts 13, 14, and 21-24. In addition, FIG. 6 shows present invention endoscope 93 components 71-74, which can represent cameras, light sources, and other devices or systems appropriate to the intended application. FIG. 7 is a view of the most preferred embodiment of the present invention similar in content to that shown in FIG. 6, but rotated 90-degrees from the illustration in FIG. 6. Additional imaging, diagnostic, or therapeutic features, or the features 71-74 in FIGS. 6 and 7, preferably comprise a half-cylinder shape with a smooth arcuate perimeter that facilitates use of the present invention device in medical applications through an endoscopic port, or are otherwise configured to fit into a housing or casing in the shape of a half-cylinder. However, a circular cross-sectional configuration is not critical, particularly for non-medical applications, and it is also considered to be within the scope of the present invention for the combined configuration of imaging probe 19, cameras 71 and 73, and light sources 72 and 74, and additional imaging, diagnostic, or therapeutic feature or features (not shown) to be that of an ellipse, half-hexagon, half-octagon, or other polygonal shape with angles of approximately 60-degrees or less, or any other shape that will fit the diagnostic/sensors probes and/or the therapeutic or any control features needed for the application and still fits the entry port for the space or cavity. FIG. 7 further shows the components 100 and 101 that may comprise one or more wires for imaging probes 19 or 20 to transmit electricity and data from/to a a camera or system (71 or 73) and/or a light source or other system/device (72 or 74). Although not shown, components 100 and 101 may also encase tubing that transmit fluids for irrigation of at least one component of said endoscopic device 93 or a visual target 94.

FIG. 8a is a sectioned view of a portion of the gearbox backbone 65 in the most preferred embodiment of the present invention showing the portions of the first, second, and third movement transmitting means associated with gearbox backbone 65. In contrast, FIG. 8b is an enlarged view of a portion of the third movement transmitting means shown in FIG. 8a, which more clearly shows the configuration, positioning, and engagement of several gears (46, 48, and 49) and pulley stops (104 and 105) in their association with the rod depending from the probe arms adjust button 58. In addition, FIG. 9 is an exploded view of the portion of the most preferred embodiment of the present invention in its gearbox casing 66 that relate to the control means and the convergence adjust button with elongated rod 59 (the rod is not separately numbered) that is used for manual convergence of first and second imaging probes (19, 20) during selection of a visual target 94. For further explanation of the interrelationship and functions of the components in FIGS. 8a, 8b, and 9, see FIG. 2b, and FIGS. 13a-15c, and invention descriptions provided above in paragraphs [0064]-[0086]. Imaging probes 19 and 20, as well as movable probe arms 9 and 10, are typically positioned adjacent to one another in a closed arrangement prior to insertion of the distal end of main tubular shaft 1 into a cavity opening, such as but not limited to a endoscopic port (not shown). For creating a 3-dimensional effect, at least two imaging probes 19 and 20 must be the same kind, and one of the same kind imaging probes 19 must be mounted onto probe arm 9 with the other same kind imaging probe 20 mounted on probe arm 10. It is contemplated for imaging probes 19 and 20 in the present invention to include, but not be limited to, cameras, ultrasound devices, and other imaging sensors (see component list above for additional examples). Imaging probes 19 and 20 are mounted to the distal end of a different probe arm 9 or 10, with the proximal ends of the two probe arms 9 and 10 movably mounted on the distal tip of main tubular shaft 1 (see FIGS. 4-7, and 20) so as to provide simultaneous movement of both probe arms 9 and 10 in opposed directions toward and away from one another within an approximate 180-degree angle range of movement (an approximate 90-degree range of movement for each probe arm 9 and 10). It is the resulting side-to-side movement of the probe arms 9 and 10 within a 180-degree angle range of movement (to and from the fully closed position where the imaging probes 19 and 20 are positioned adjacent to one another) that creates a change in the distance between imaging probes 19 and 20 axes that can be adjusted to the average intra-pupillary distance of approximately 5-7 cm found between human eyes, thereby allowing the imaging probes 19 and 20 to have depth perception equivalent to that of human eyes (for similar sized objects positioned at similar distances from the human eyes). The ability to adjust the distance between the probe arms 9 and 10 at any time also gives the operator variability for navigating in small, narrow, and irregularly-shaped spaces inaccessible by the unaided human eye, while at the same time providing the operator (not shown) an option to move the imaging probes 19 and 20 further apart at most of the probe arm 9 and 10 positions to enhance depth perception for a closer and more detailed look at any feature or object encountered (not shown, other than as the visual target 94 identified in the schematic representation of FIG. 19). Another feature of the present invention is convergence which is dynamic and can be achieved through dynamic positioning adjustments of imaging probes 19 and 20 on probe arms 9 and 10 which is typically done by semi-automated or fully automated means that are explained in detail later on. The image from one imaging probe (either 19 or 20) is transmitted to a display system seen by one of the operator's two eyes, with the image from the remaining imaging probe 19 or 20 being transmitted to a display system seen by the second operator eye, wherein the independent display systems in front of each operator eye can be incorporated using a computer system into the images transmitted to the same headmounted video system, 3-D eye glasses, 3-D monitor, 3-D projector, 3-D eye pieces incorporated in a console (not shown), 3-D display 89, but not limited thereto. Further, imaging (such as ultrasound images) from multiple additional imaging features 71-74 and 88 can be superimposed on corresponding images (such as a camera image) from imaging probes 19 and 20, according to operator preference or need. The creation of a visual target 94 image requires light, which can also be provided by the present invention via fiber-optics or LED's (used only as examples and not limited thereto), or any other light source that has the compact configuration needed for being mounted adjacent to the imaging probes 19 and 20 on the distal ends of the probe arms 9 and 10 (and entry into the small openings typically encountered when entering a visual target 94 viewing area, while also having the capability of producing the needed amount of light for imaging probe 19 and 20 use with minimal heat generation.

Prior to manufacture of a present invention endoscopic device 93, the applications for which it is to be used must be evaluated and a determination made as to the maximum distance anticipated from the distal tip of the main tubular shaft 1 to most visual targets 94. Using this information, and other information such as that relating to imaging probe pulley/gear size, calculations may be made to determine the ratio of convergence needed for any visual target 94 at any specified distance from the present invention endoscopic device 93. An average ratio of convergence can then be calculated upon which to base selection of an appropriate set of gears and pulleys (one example includes those shown secured to the gearbox backbone 65 in FIG. 8a) that are needed to achieve the appropriate reduction of the slider 6 linear movement for turning the imaging probe pulley-like structures 103 (see FIG. 3) sufficiently to obtain imaging probe 19 and 20 convergence. Prior to using a semi-automated configuration of the present invention in a specific application and selecting a set of multiple gears and pulleys with a predetermined ratio of convergence appropriate to the amount of convergence anticipated for the application, one would need to estimate the distance from the present invention endoscopic device 93 at the primary/original position (at the slider 6 ZERO point) to the farthest possible visual target 94 anticipated in the application, or within the cavity that the present invention endoscopic device 93 will be primarily used, and accordingly calculate the ratio of convergence for this visual target 94 distance as previously described above. In fully-automated configuration, although a set of multiple gears and pulleys with a pre-determined ratio of convergence is also used, the computer component 92 will dynamically calculate the ratio of convergence each time the present invention endoscopic device 93 moves, and from the continually changing information it receives from multiple position sensors 88 (or other), computer 92 will activate a motor 91 to make the appropriate adjustments in convergence for imaging probes 19 and 20.

On the left side of FIG. 8a, one sees the large dual groove pulley 40 with associated helical gear 41 in front of the interior surface of the gearbox backbone 65. The external teeth of helical gear 41 are in working engagement with the external helical teeth 37 of the slider-related helical gear 35, which is axially aligned in vertical arrangement with several other present invention components. Above and outside the top exterior surface of gearbox backbone 65, one sees the convergence adjust button with elongated rod 59 that is used for manual convergence of first and second imaging probes 19 and 20, the reset button with rod 42 used to engage/disengage the first and second movement transmitting means, and the probe arms adjust button 58 for opening and closing probe arms (9, 10). Below the slider-related helical gear 35, one sees the external teeth 62 of imaging probes convergence-related gear 39. FIGS. 13a-15c in paragraphs [0084]-[0086] show additional views, including sectioned views, of the slider-related helical gear 35, imaging probes convergence related gear 39, reset button 42, and the springs 32 and 54 used with them. As seen more clearly in FIG. 9, has a reset button with rod 42 with a ring 43 at its distal end. Also, the elongated rod depending downwardly from the convergence adjust button 59 in FIG. 9 is inserted through the central opening in the convergence mechanism core rod 57, which has external side teeth 61 on a portion of its exterior surface. As further shown in FIG. 9, one end of the convergence mechanism core rod 57 has external top teeth 60 that are configured to engage the bottom teeth 31 on convergence adjust button 59. The end of convergence mechanism core rod 57 remote from external top teeth 60 is enlarged (no separate number), and during use is positioned between and against spring 54 and the ring 43 at the distal end of reset button with rod 42. The small spring 27 shown in FIG. 9 is axially aligned with the elongated rod depending downwardly from the convergence adjust button 59, and during use is positioned between and against external top teeth 60 and the bottom teeth 31 on convergence adjust button 59. As further shown in FIG. 9, the external side teeth 61 on the convergence mechanism core rod 57 move up and down in response to movement of reset button 42 from a position where external side teeth 61 extend through both slider-related helical gear 35 and imaging probes convergence-related gear 39, engaging the first and second movement transmitting means, to a position where external side teeth 61 extend only through imaging probes convergence-related gear 39, causing disengagement of the the first and second movement transmitting means. Above slider-related helical gear 35 and imaging probes convergence-related gear 39 in FIG. 9 one sees a spring 33 and its associated slider-related locking gear 32 in the convergence mechanism combination, which locks slider-related helical gear 35 during manual convergence of imaging probes (19, 20) initiated by the convergence adjust button 59 after the introduction of main tubular shaft 1 into a cavity while choosing (converging on) a visual target 94. Finally, FIG. 9 shows the bushing/brackets without teeth (34, 77) and the bushing/bracket with internal teeth 76 that are fixed to gearbox backbone 65 and used to mount the convergence mechanism combination, including the slider-related locking gear 32 while it assists in stopping slider-related helical gear 35 during manual convergence of imaging probes (19, 20) initiated by the convergence adjust button 59. Bushing/brackets 34, 77, and 76 are also shown in FIG. 8a in close association with reset button 43, slider-related helical gear 35, and imaging probes convergence-related gear 39.

FIGS. 8a and 8b also show portions of the first and second movement transmitting means, including the dual gear with pulley 46/48 related to imaging probes (19, 20) convergence. Although obscured in FIG. 8a by reset button 42, the external teeth of large gear 46 are in working engagement with the external teeth 62 of imaging probes convergence-related gear 39. The smaller diameter dual gear has the number 48, and the pulley associated with gear 48 has the number 78. In Fig. Sa a flat coiled spring 75 is positioned below, and associated with, the larger gear 46, and used for returning imaging probes (19, 20) to their neutral position where they are parallel to one another (without convergence). FIGS. 8a and 8b further show a second small gear with pulley 49 that is also related to imaging probes convergence and has external teeth in working engagement with the external teeth of the small gear 48 positioned next to it. The pulley associated with gear 49 is separately identified by the number 79 in FIG. 16b. Also shown in FIG. 8a in a position above gears 48 and 49 is another flat coiled spring 69 used to return the probe arms adjust button 58 (opens and closes probe arms 9, 10) to the neutral position, and place probe arms (9, 10) in their closed position adjacent to one another. Although shown in unmarked form in FIG. 8a, but identified by numbering in FIG. 8b, FIGS. 8a and 8b show the pulley stops (104, 106) and opposing pulley stops (105, 107) that limit the combined movement of probe arms (9, 10) away from one another to approximately 180-degrees. Lastly, FIG. 8a shows three unnumbered bushings/brackets connected to gearbox backbone 65 for support of present invention components related to imaging probes (19, 20) convergence, one below flat coiled spring 75, one above flat coiled spring 69, and the other supporting the dual groove pulley 30 related to probe arms adjust button 58 and used with cable/belt extensions (52, 53) and cables/belts 23,24 (not shown in FIG. 8a, but visible in FIG. 17a) employed for opening and closing probe arms (9, 10). The four path guide pulleys (marked by the numbers 55 and 56 in sets of two) are also shown in FIG. 8a, which are used respectively with cable/belt extension 45 (not numbered in FIG. 8a, but shown in FIG. 12a,b) and cable/belt extension 44 and transmit movement of slider 6 received from slider cable/belt 8 to the large dual groove pulley 40 with associated helical gear 41.

FIG. 10 is an enlarged view of the same components previously discussed and shown in the top portion of FIG. 1, while FIG. 11 is a transparent view of the slider 6 and main tubular shaft 1 in the most preferred embodiment of the present invention endoscope 93 showing preferred placement of belt/cable 8 and pulleys 7 and 26 related to slider 6 movement on the main tubular shaft 1. FIGS. 12a-12d also relate to transmission of slider 6 movement, and are perspective views of components used as a part of the first movement transmitting means in the most preferred embodiment of the present invention endoscopic device 93, including large dual groove pulley with helical gear 40, slider 6, cables/belts 8 and cable/belt extensions 44 and 45, and guide pulleys 7, 26, 55, and 56. FIG. 12b is an enlarged view of the large dual groove pulley with helical gear 40 shown in FIG. 12a having cables/belts 44 and 45 connected to different pulley winding grooves, while the helical gear with external teeth 41 associated with large dual groove pulley 40 remains available for engagement with the helical external teeth 37 of slider-related helical gear 35 (see FIG. 8a). FIG. 12c is an enlarged view of the slider 6 shown in FIG. 12a, with a belt/cable 8 used for slider 6 movement attached to one side of the interior rail assembly 70 in slider 6. FIG. 12d shows a roller 99 that can be used with the slider 6 shown in FIG. 12c to assist slider 6 movement on the main tubular shaft 1, or in one or more channels 2 on main tubular shaft 1.

FIGS. 13a-c, 14a-c, and 15a-c illustrate the control means of the present invention endoscopic device 93 in association with the first and second movement transmitting means, and also with the manual convergence means, in three positions of engagement and disengagement. In the present invention, the first and second movement transmitting means will each always have at least one integrated movement element shared with the control means, the shared integrated movement element acting as an intermediary, assisting in the controlling of engagement and disengagement of the first and second movement transmitting means to/from one another. Although not limited thereto, two examples of shared integrated movement elements of the first movement transmitting means in endoscopic device 93 are its slider-related helical gear 35 and its large dual groove pulley 40 with associated helical gear 41, while two examples of shared integrated movement elements of the second movement transmitting means in endoscopic device 93 are imaging probes convergence-related gear 39 and the dual gear with pulley 46 related to imaging probes (19, 20) convergence. See above paragraphs [0064]-[0076] for additional disclosure relating to the control means in the most preferred embodiment of endoscopic device 93.

FIGS. 13a-c are side views of the control means associated with the gearbox casing 66 in the most preferred embodiment of the present invention endoscope 93 showing convergence mechanism core rod 57 in its position of use with the first and second movement transmitting means disengaged. In contrast to FIG. 13a, FIG. 13b is a sectioned view of the invention structure in FIG. 13a, which shows the external teeth 61 of convergence mechanism core rod 57 only engaging the internal teeth 38 of imaging probes convergence related gear 39 for first and second movement transmitting means disengagement. FIG. 13b also more clearly shows the slider-related locking gear 32 disengaged from the slider-related helical gear 35 with external teeth. FIG. 13c is a sectioned view of the invention structure shown in FIG. 13b, except the convergence mechanism core rod 57 and slider-related locking gear 32 have been removed to reveal the internal teeth 38 in the imaging probes convergence-related gear 39, the internal teeth 36 in the slider-related helical gear 35, and the internal teeth (not separately numbered) in a bushing/bracket 76 fixed to the gearbox backbone 65. FIGS. 13a-c each further show the reset button 42 supported by bushing/bracket 76 that is secured to the interior surface of gearbox backbone 65, and reset button 42 with downwardly depressed positioning.

FIGS. 14a-c are side views of the control means associated with the gearbox casing 66 in the most preferred embodiment of the present invention endoscope 93 showing convergence mechanism core rod 57 in its position of use with the first and second movement transmitting means engaged. In contrast to FIG. 14a, FIG. 14b is a sectioned view of the invention structure in FIG. 14a, which shows the external teeth 61 of convergence mechanism core rod 57 engaging the internal teeth 36 of the slider-related helical gear 35 and the internal teeth 38 of the imaging probes convergence-related gear 39 for first and second movement transmitting means engagement. FIG. 14b also more clearly shows the slider-related locking gear 32 disengaged from the slider-related helical gear 35. FIG. 14c is a sectioned view of the invention structure shown in FIG. 14b, except the convergence mechanism core rod 57 and slider-related locking gear 32 have been removed to reveal the internal teeth 38 in the imaging probes convergence-related gear 39, the internal teeth 36 in the slider-related helical gear 35, and the internal teeth (not separately numbered) in a bushing/bracket 76 fixed to the gearbox backbone 65. FIGS. 14a-c each further show the reset button 42 supported by bushing/bracket 76 backbone, the reset button 42 now with upward positioning as compared to that shown in FIG. 13a.

FIGS. 15a-c are side views of the control means associated with the gearbox casing 66 in the most preferred embodiment of the present invention endoscope 93 showing convergence mechanism core rod 57 in its position of use with the first and second movement transmitting means disengaged, and also showing the slider-related locking gear 32 engaging the slider-related helical gear 35 with external teeth 37. In contrast to FIG. 15a, FIG. 15b is a sectioned view of the invention structure in FIG. 15a, which shows the external teeth 61 of convergence mechanism core rod 57 only engaging the internal teeth 36 of imaging probes convergence related gear 35 and the bottom teeth 31 of convergence adjust button 59 engaging external top teeth 60 of the convergence mechanism core rod 57 for manual convergence of imaging probes 19 and 20, or others of the same kind to locate a visual target 94. FIG. 15b also more clearly shows the slider-related locking gear 32 engaging the slider-related helical gear 35 with external teeth 37 to lock it in place. FIG. 15c is a sectioned view of the invention structure shown in FIG. 15b, except the convergence mechanism core rod 57 and slider related locking gear 32 have been removed to reveal the internal teeth 38 in the imaging probes convergence related gear 39, the internal teeth 36 in the slider-related helical gear 35, and the internal teeth (not separately numbered) in a bushing/bracket 76 fixed to the gearbox backbone 65. FIGS. 15a-c each further show reset button 42 supported by bushing/bracket 76, and in a downwardly depressed position similar to that in FIG. 13a.

FIGS. 16a-d are perspective views of components used as a part of the second movement transmitting means in the most preferred embodiment of the present invention endoscopic device 93, which include large dual gear with pulley 46/48, small gear 49, imaging probes (19, 20), pulleys 11 and 12, pin 4, and cables/belts 13, 14, 21, 22, and cable/belt extensions 51. FIG. 16*b* is enlarged view of the large dual gear (larger/smaller gear combination 46/48) with pulley 46 shown in FIG. 16*a* that is related to imaging probes (19, 20) convergence. FIGS. 16*a* and 16*b* also show the exterior teeth of small gears 48 and 49 in working engagement with one another. The pulleys 78 and 79, respectively, on small gears 48 and 49, have cable/belt 51 windings in opposing directions so that imaging probes 19 and 20 move in opposite directions toward and away from one another for convergence and divergence, and not in the same direction back and forth while remaining substantially parallel to one another. In contrast, FIG. 16*c* is a perspective view of a pair of dual groove pulleys 11 and 12 each with with a cable crimp sleeve 28 partially covering the cables/belts 13, 14, 21, 22 in the most preferred embodiment of the present invention used to fix cables/belts (such as but not limited to cables/belts 21 and 22) respectively, to their corresponding winding grooves on pulleys (such as but not limited to pulleys 11 and 12). FIG. 16*d* is a perspective view of a single dual groove pulley with cable crimp sleeve in the most preferred embodiment of the present invention similar to those shown in FIG. 16*c*.

FIGS. 17*a*-*c* are perspective views of the third movement transmitting means used in the most preferred embodiment of the present invention to open and close probe arms 9 and 10. FIG. 17*a* shows the probe arms adjust button 58 having a thin diameter rod extending there from in one direction, which is used as an axle to support a dual groove pulley 30 within gearbox casing 66. As is further shown in FIG. 17*a*, a cable/belt extension 52 engages one of the side-by-side grooves of dual groove pulley 30, and extends between pulley 30 and the cable/belt 23 connected to a pulley on the proximal end of the first probe arm 9. Similarly, a cable/belt extension 53 engages the other one of the side-by-side grooves of dual groove pulley 30, and extends between pulley 30 and the cable/belt 24 connected a pulley on the proximal end of the second probe arm 10. While FIG. 17*a* shows cable/belt extension 52 and cable/belt 23 combination having the configuration of a simple loop, the configuration of the cable/belt extension 53 and cable/belt 24 combination is crossed over itself and shown in the shape of a figure-8. This combination structure wherein one cable/belt has a figure-8 configuration, while the other cable/belt is a simple loop, assures synchronous movement of the connected imaging probes 9 and 10 in opposed directions. FIG. 17*a* further shows the first imaging probe 19 supported for convergence rotation by the distal end of the first probe arm 9, and the second imaging probe 20 supported for convergence rotation by the distal end of the second probe arm 10. FIG. 17*b* is an enlarged view of the probe arms 9 and 10 prepared for mounting on the distal end of the main tubular shaft 1. In FIG. 17*b* the number 102 identifies the pulley-like structure that is present on the proximal end of each of the two probe arms, 9 and 10, and respectively engage cables/belts 23 and 24. Referring to FIG. 3 will help to identify other present invention components shown in FIG. 17*b*, including the pin 4 which serves as an axle for the opening and closing rotation of probe arms 9 and 10, and the small hinge 29 on each probe arm 9 and 10 located adjacent to the pulley-like structure present on the proximal end of probe arms 9 and 10. FIG. 17*b* also shows the imaging probes 19 and 20 connected to probe arms 9 and 10, with the pair of imaging probes 19 and 20 in a parallel orientation that represents a non-converged/neutral condition. In contrast, FIG. 17*c* reveals the preferred configuration of the hinge 80 at the distal end of first probe arm 9 providing a moving connection of the first imaging probe 19 to probe arm 9. As is shown in FIG. 3, the second probe arm 10 has a similar hinge 80 providing a moving connection of the second imaging probe 20 to probe arm 10.

FIGS. 18*a* and 18*b* are respectively perspective and side views of an alternative sturdy, non-slip pulley/cable system 81/84 that can be used as a part of the most preferred embodiment of the present invention endoscopic device 93 when a high level of accuracy in transmission of movement is required. It can be used in place of any belt and gear combination that provides outward and return movement to one location. It is shown in part in the present invention large dual groove pulley 40, and can also be used as part of the structure in other present invention pulleys. FIG. 18*a* shows the first dual groove pulley 81 engaged to second dual groove pulley 84 by two sets of cables, first cable 82 and second cable 83. The dual groove pulleys 81 and 84 have one portion of their perimeter edges facing one another, so that when viewed from the side, as in FIG. 18*b*, the left groove of pulley 81 is aligned with the left groove of pulley 84, and the right grooves of pulleys 81 and 84 are also similarly aligned. The number 85 in FIG. 18*a* represents the attachment locations for fixing the ends of cables 82 and 83 to the left and right independent winding grooves in the first dual groove pulley 81. Similarly, number 86 in FIG. 18*a* represents the attachment locations for fixing the opposing ends of cables 82 and 83 to the left and right independent winding grooves in the second dual groove pulley 84. As is more clearly visible in FIG. 18*b*, one end of each cable (82 and 83) is fixed to first dual groove pulley 81 and the opposing end of cable (82 and 83) is fixed to second dual groove pulley 84, with each cable 82 and 83 rolled in an opposing direction from the other, so that as one cable (82 or 83) unrolls and leaves its groove on pulley 81 or 84, the other cable (82 or 83) will rollup and become increasingly added to its groove on the opposing pulley 81 or 84. This pulleys/cables system can be used to prevent slippage, provide more precision and accuracy, and/or provide a stronger system for high stress applications, and can be comprise gear teeth (not shown) to allow it to engage other gears whether linear or circular. The thickness of cables 82 and 83 relative to the diameter dimensions of pulleys 81 and 84, as well as the position and shape of the pulleys 81 and 84, should not be considered as limiting, and may be different from that shown in FIGS. 18*a* and 18*b*. This particular pulley system configuration shown in FIGS. 18*a* and 18*b* is used when high level of accuracy in transmission of movement is required because it is configured to minimize chances of slipping between the pulleys (81 and 84) and the cables (82 and 83) connected to them, also when an exact limited numbers of revolutions and turns of the gear system are required for the application (which is controlled by the number of loops that the cable is looped on each pulley 79 and 80 at the time the pulley system was made before its initial usage). To prepare first double pulley 81 and second double pulley 84 for use, one end of a first flexible but non-stretchable cable 82 is anchored to first double pulley 81 adjacent to one of its winding grooves and then looped around the adjacent winding groove a pre-determined number of times. First double pulley 81 is then aligned with second pulley 84 and placed at the needed spaced-apart distance from second pulley 84 dictated by the application. After first flexible but non-stretchable cable 82 is extended across the spaced-apart distance to second pulley 84, it is looped the same pre-determined number of times around the opposed winding groove in second pulley 84, after which it is anchored to second double pulley 84. A second flexible but non-stretchable cable 83 is similarly anchored and looped around the unused set of opposed independent winding grooves in double pulleys 81 and 84. Since cables 82 and 83 do not stretch, springs would provide any needed bias in the connection (not shown). It is contemplated for attachment points 85 and 86 to be merely representative. As a result, the size and relative position for attachment points 85 and 86 shown in FIGS. 18a and 18b on first double pulley 81 and second double pulley 84 should not be considered limiting.

FIG. 19 is a not-to-scale schematic view of a partially or fully automated embodiment of the present invention 3-D endoscope 93 during use in a medical application when a very high level of convergence accuracy is continuously needed in imaging probes 19 and 20 for certain applications. It shows the present invention endoscopic device 93 near a visual target 94 with its probe arms 9, and 10 in an opened configuration and imaging probes 19 and 20 in a converged configuration in front of visual target 94. It also shows a unit 88 that can be used as a laser pointer, an endoscope-to-target distance sensor, or both, or another system or device (see Component List for examples). In addition, FIG. 19 shows a representation of wireless receiver/transmitter 96 associated with the present invention 3-D endoscope 93, and representations of wireless receiver/transmitters 97 and 98 respectively associated with a visual display system 89 and a robotic system 90, one of the arms, tools, or connections thereof shown associated with the end of the present invention 3-D endoscope 93 remotely located from probe arms 9 and 10. FIG. 19 also shows a representation a computer component 92 and an electric motor 91 that can be used together to initiate automated convergence adjustment of imaging probes 19 and 10, as well as 3-D endoscope functions control in integration with robotic systems 90. Communication via wireless receivers/transmitters 96-98 in partially or fully automated embodiment of the present invention 3-D endoscope 93 allow feedback to a computer 92 for continuous monitoring and convergence to specifications pre-determined by an operator, until the operator no longer needs automated convergence to occur.

FIG. 20 is an enlarged view of the probe arms (9, 10) of the most preferred embodiment of the present invention endoscopic device 93 in a partially opened position and an endoscope-to-target distance sensor or laser pointer 88 mounted centrally on the same pin 4 from which the probe arms (9, 10) pivot. Similar to FIG. 17a, imaging probes (19, 20) are in a converged configuration and not parallel to one another. In addition to use as a laser pointer or a positioning sensor for determining changes in endoscope-to-target distance, unit 88 may serve other useful functions, with the above Component List providing some examples, including providing maintenance improving characteristics and a simple assist in the alignment of the longitudinal axis of the main tubular shaft 1 with visual target 94 during the initial manual convergence of imaging probes 19 and 20 in an efficient and rapid manner using the rotatable manual convergence adjust control 59. In contrast, when unit 88 is used as an endoscope-to-target distance sensor in a fully automated configuration of the present invention endoscope 93, unit 88 provides a computer component 92 the information needed for calculation of the amount of convergence needed for imaging probes 19 and 20. When unit 88 is mounted on the same axis as probe arms 9 and 10, it is preferred for the proximal end of endoscope-to-target distance sensor or laser pointer 88 to have a complementary configuration to the other present invention components, so that all complement one another to minimize the diameter dimension of the distal end of main tubular shaft 1 for medical applications. It is important but not critical for convergence calculations that target distance sensor 88 be mounted centrally on the distal end of the main tubular shaft 1. The relative size and configuration of target distance sensor or laser pointer 88, as compared to that of imaging probes (19, 20) and probe arms (9, 10) is merely representative in FIG. 20 and configurations and sizes other than that shown are also contemplated. Although not shown, another application of unit 88 in the same or a different size or configuration is as a positioning sensor associated with the exterior surface of the main tubular shaft 1, or a channel 2 in the exterior surface of the main tubular shaft 1 in fully or partially automated embodiments of the present invention endoscope 93. Also, depending upon its function, unit 88 may be activated upon the opening of probe arms 9 and 10. FIG. 20 also shows a camera 71 and two light sources on the distal end of imaging probe 20, and cables/belts 13 and 14 used for transmitting convergence movement respectively to second and first imaging probes 20 and 19, in addition to the path guide pulleys 15 and 17 respectively for first and second cables/belts 13 and 15, plus the pin 18 for mounting path guide pulley 17 to hinge 29 on the second probe arm 10. It is also contemplated for any of the imaging probes (19, 20), unit 88, cameras (71, 71), and light sources (72, 74) to have a non-permanent connection to said present invention 3-D endoscope 93 and be interchangeable within the same medical or non-medical procedure, or between applications. Also optionally, although not limited thereto, the present invention endoscope 93 may have one or more maintenance improving characteristics, such as maintenance-related features or characteristics helping to keep at least part of the endoscopic device 93 in good working order, materials that decrease fogging, tools and/or materials decreasing body fluid smudging, systems transmitting fluids for irrigation of at least one component of endoscopic device 93, materials preventing tissue sticking to at least one component of endoscopic device 93, systems and/or materials providing lubrication, fluid repellant materials, and systems assisting in sterilization of at least one part of endoscopic device 93. Unit 88 may provide at least one of the sources for needed maintenance-related features or characteristics.

INDUSTRIAL APPLICABILITY

This invention is an improved endoscopic device 93 for obtaining 3-dimensional human vision simulated imaging with real dynamic convergence in therapeutic, diagnostic, and other applications. Imaging probes (19, 20) are mounted on probe arms (9, 10) that are in turn mounted on a tubular shaft 1 and a simple/sleek slider 6 moves back-and-forth on the shaft 1, with slider 6 movement optionally modified and redirected to affect imaging probes (19, 20) convergence/divergence. Imaging probes (19, 20) convergence/divergence can be optionally manual for visual target 94 selection, and the probe arms (9, 10) upon which the imaging probes (19, 20) are mounted may also be moved toward and away from one another through a combined 180-degree movement range using a manual control 59. The first and second movement transmitting means respectively adapted to cause slider-initiated convergence, or manual convergence, of the imaging probes (19, 20) each share at least one integrated movement element with the control means adapted for engaging and disengaging the first and second movement transmitting means. The present invention endoscope 93 can be fitted with different diagnostic and therapeutic systems, and can be adapted to work with robotic systems 90. Also, in conjunction with slider 6 movement, or in the alternative, endoscope 93 positioning information determined with or without an endoscope-to-target distance-sensor 88, in addition to changes in endoscope-to-target distance and the endoscope's relative position to a visual target 94 otherwise determined, can be used by a computer component 92 for fully automated imaging probe (19, 20) convergence.

The improvements herein provide more sophistication, make the endoscopic device 93 less fragile and more user-friendly, allow easier control during applications, and it has fewer external moving parts that reduce contamination risk, which is especially important in surgical applications. It is also simpler in design than comparable prior art, lowering manufacturing cost. No other endoscopic system and method adaptable for therapeutic and non-medical applications, as well as sensor/diagnostic operation, is known with the same structure, to provide all of the benefits and advantages of the present invention endoscopic device 93, or function in the same manner as the present invention to provide real dynamic convergence flexibility in spaced-apart probe distance adjustment that facilitates imaging probe (19, 20) use in a larger variety of applications and in different types of cavities or spaces while simultaneously giving its operator superior depth perception.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. An endoscopic apparatus for producing three dimensional images having dynamic convergence, the apparatus comprising:
   a main tubular shaft coupled to a gearbox;
   a slider configured to slide along the main tubular shaft;
   a first probe arm and a second probe arm hingedly coupled to the main tubular shaft and configured for a combined 180-degree range of movement;
   at least two imaging probes coupled individually to the first probe arm and the second probe arm, each imaging probe having a longitudinal axis, and being movably secured to the first probe arm and the second probe arm in a manner resulting in a convergence of the imaging probes such that the imaging probes provide a 3-dimensional simulated human vision imaging with dynamic convergence;
   the gearbox coupled to the main tubular shaft opposite the first probe arm and the second probe arm, and configured for a reducing movement;
   a slider mechanism, the slider mechanism configured to transmit to the gearbox back and forth longitudinal movement of the slider relative to the main tubular shaft;
   a convergence adjustment, the convergence adjustment configured to transmit to the imaging probes back and forth longitudinal movement of the slider affecting the convergence after the reducing movement;
   a probe arm mechanism configured to open and close the first and second probe arms;
   a controller engaging and disengaging the slider mechanism and convergence adjustment, wherein when the slider mechanism and convergence adjustment are engaged, linear movement of the slider, after the reducing movement, is transmitted to the imaging probes for convergence; and
   wherein the slider mechanism comprises a first integrated movement element, and the convergence adjustment has a second integrated movement element, wherein the controller is biased to a first position wherein both the first integrated movement element and the second integrated movement element are engaged, and wherein the controller movable to a second position such that the second integrated movement element is engaged while the first integrated movement element is disengaged, whereby the 3-dimensional human vision simulated imaging with dynamic convergence is achieved.

2. The endoscopic device of claim 1 wherein the slider mechanism comprises a first gear having a first axis, external teeth, and internal teeth, and wherein the external teeth transmit movement from the slider mechanism; wherein the convergence adjustment comprises a second gear having a second axis, external teeth, and internal teeth, and wherein the external teeth transmit movement to the convergence adjustment; wherein the first and second gears are axially aligned with one another; wherein the controller is further characterized by an elongated convergence mechanism core rod having a circumference and external teeth on a portion of the circumference, the convergence mechanism core rod axially aligned with the first gear and the second gear and configured to move back and forth along an axis common to the first axis and the second axis inside the first gear and the second gear, the external teeth of the convergence mechanism core rod engaging the internal teeth of the second gear and the first gear; wherein movement of the convergence mechanism core rod in one direction by a predetermined distance causes the external teeth of the convergence mechanism core rod to engage the internal teeth of both the first and second gears, thereby engaging the slider mechanism and the convergence adjustment and allowing any movement of the slider mechanism to be transmitted to the convergence adjustment, and further wherein movement of the convergence mechanism core rod in an opposing direction by a predetermined distance allows the external teeth of the convergence mechanism core rod to engage only the internal teeth of the second gear related to said convergence adjustment and causing disengagement of the first gear, disengaging the slider mechanism and convergence adjustment and allowing the slider mechanism and convergence adjustment to move independently from each other.

3. The endoscopic device of claim 2 wherein the controller is further characterized by a rotatable manual convergence adjust button with an internal axis and circumferentially positioned bottom teeth, and further characterized by a convergence mechanism core rod further comprising an internal axis and circumferentially positioned top teeth, the internal axis being axially aligned with the convergence mechanism core rod, such that the manual convergence adjust button and the convergence mechanism core rod rotate in tandem when the manual convergence adjust button is pushed down and the bottom teeth of the manual convergence adjust button engage the top teeth of the convergence mechanism core rod; and during in tandem rotation, the external teeth of the convergence mechanism core rod engage only the internal teeth of the second gear, causing rotational movement of the manual convergence adjust button to be transmitted to the imaging probes by the convergence adjustment, thereby allowing manual convergence of the imaging probes on selected visual targets.

4. The endoscopic device of claim 3 wherein the controller comprises at least one bracket fixed to the gearbox and a slider-related locking gear, the slider-related locking gear in selective working engagement between the rotatable manual convergence adjust button and the internal teeth of the first gear to lock the first gear to the gearbox by the at least one bracket, thereby preventing movement of the first gear during manual convergence of the imaging probes for selection of a visual target.

5. The endoscopic device of claim 3 wherein the controller is configured to disengage the slider mechanism and convergence adjustment from each other, the controller comprising a reset button in selective working engagement with the convergence mechanism core rod, wherein the external teeth of the convergence mechanism core rod only engage the internal teeth of the second gear when the reset button is pushed, allowing both the first and second movement transmitting means to move independently from each other and the imaging probes to return to a neutral position in parallel to each other.

6. The endoscopic device of claim 1 further characterized by pulley stops and opposing pulley stops configured to limit combined movement of the first and second probe arms away from one another to approximately 180-degrees.

7. The endoscopic device of claim 1 wherein the controller is further characterized by at least one computer component, at least one motor, at least one pulley, at least one gear, and at least one sensor means adapted for detecting positioning of the endoscopic device relative to a target object, the at least one computer component in communication with the at least one sensor means and the at least one motor, the at least one computer component configured to use positioning data detected by and received from the at least one sensor means to determine the amount of convergence needed in the imaging probes, and to activate the at least one motor to accurately cause a needed amount of convergence in the at least two imaging probes.

8. The endoscopic device of claim 1 further characterized by at least one wireless receiver and at least one wireless transmitter each having at least one function selected from the group consisting of wirelessly transmitting data from and to the imaging probes, wirelessly transmitting control commands between at least one computer component, the endoscopic device to control at least one function of the endoscopic device, wirelessly transmitting control commands between the at least one computer component and the at least one motor, wirelessly supplying the endoscopic device with power, wirelessly charging at least one power storage device in the endoscopic device, wirelessly transmitting power to at least one power receiving devices in the endoscopic device, wirelessly transmitting control commands to at least one therapeutic devices in the endoscopic device, wirelessly transmitting data between at least one position sensor and the at least one computer component, and wirelessly transmitting data from endoscopic device to at least one display device.

9. The endoscopic device of claim 1 comprising at least one aperture leading to at least one channel allowing introduction and use of at least one independent instrument concurrently with the endoscopic device inside the cavity where the endoscopic device is inserted.

10. The endoscopic device of claim 1 comprising at least one robotic system and wherein at least part of the controller and at least part of a mechanism for the reducing movement are housed outside of the gearbox.

11. The endoscopic device of claim 1 wherein the convergence adjustment is further characterized by a spring configured for returning the imaging-probes to a neutral position where they are parallel to one another upon disengagement of the slider mechanism and convergence adjustment.

12. The endoscopic device of claim 1 wherein the main tubular shaft comprises an exterior surface having at least one channel and the slider is coupled to at least one component selected from in a group consisting of rollers and rail shaped structures fitting within at least one channel.

13. The endoscopic device of claim 1 comprising at least one cable guided by at least one guide-path pulley coupled to the slider, the cable configured to facilitate a longitudinal movement of the slider back and forth along the exterior surface of the main tubular shaft, and the exterior surface of the main tubular shaft also comprising at least two openings receiving the at least one cable for movement of the at least one cable within the main tubular shaft.

14. An endoscopic device for use in therapeutic, diagnostic, and other applications, for obtaining 3-dimensional human vision simulated imaging of a target object with dynamic convergence, the device comprising:

a main tubular shaft having an exterior surface, a distal end, and an opposing proximal end;

two probe arms movably mounted on the distal end of main tubular shaft for a combined 180-degree range of movement from a fully closed position wherein the probe arms are adjacent one another, the probe arms each having a distal end and a proximal end;

at least two imaging probes coupled to the probe arms, each imaging probe having a longitudinal axis, and at least two of the imaging probes being functionally identical, wherein each of the probe arms has one of the functionally identical imaging probes movably secured thereto such that convergence of the imaging probes results in 3-dimensional human vision simulated imaging;

a sensor for detecting a position of the device relative to a target object, the sensor coupled to the main tubular shaft;

at least one motor configured to assist a convergence movement of the at least two imaging probes;

at least one computer component configured to collect and analyze information regarding the position from the sensor and calculate and send to the at least one motor a corresponding amount and duration of power required to achieve convergence and divergence by the imaging probes;

a gearbox depending from the proximal end of the main tubular shaft, the gearbox configured to facilitate engagement of a slider mechanism and a convergence adjustment;

a data transmitting means configured to transmit the position of the device from the sensor to the at least one computer component;

a power transmitter configured to transmit the calculated amount and duration of power from the computer component to the at least one motor;

the slider mechanism configured to transmit movement of the at least one motor in response to a communication received from the computer component via the power transmitter to the gearbox;

the convergence adjustment configured to further transmit movement of the at least one motor from the gearbox to achieve convergence of the imaging probes;

a probe arm mechanism adapted for opening and closing the probe arms; and a controller configured to coordinate the computer component relating to activation and deactivation of the at least one motor and transmission of movement from the at least one motor through the slide mechanism to the convergence adjustment, and further to the imaging probes for convergence and 3-dimensional human vision simulated imaging.

15. The endoscopic device of claim 14 comprising at least one wireless receiver and at least one wireless transmitter, each configured to have at least one function selected from the group consisting of wirelessly transmitting data from and to the imaging probes, wirelessly transmitting control commands between the at least one computer component to control at least one function of the device, wirelessly transmitting control commands between the at least one computer component and the at least one motor, wirelessly supplying the device with sufficient power to operate, wirelessly charging at least one of power storage device in the device, wirelessly transmitting power to at least one energy receiving devices in the device, wirelessly transmitting control commands to at least one therapeutic device in the device to control its function, wirelessly transmitting data between the at least one sensor and the at least one computer component, and wirelessly transmitting data from the device to at least one display.

16. A method for producing 3-dimensional human vision simulated imaging of a target object with real dynamic convergence in therapeutic and sensor applications, wherein the target object is located behind a limited-access opening, the method comprising the steps of:
providing a target object behind a limited access opening;
providing an endoscopic device and obtaining a 3-dimensional human vision simulated image with real dynamic convergence, the device comprising:
a main tubular shaft having an exterior surface, a distal end, and an opposing proximal end;
a slider positioned for alternating back and forth movement along the exterior surface between the distal end and the proximal end;
two probe arms, each movably mounted on the distal end for a combined 180-degree range movement from a fully closed position wherein the probe arms are adjacent to each other, the probe arms each having a distal end and a proximal end;
at least two imaging probes coupled to the probe arms, each of the imaging probes having a longitudinal axis, at least two of said imaging probes being functionally identical, with each of the probe arms movably secured thereto in a manner allowing convergence of the imaging probes for providing the 3-dimensional human vision simulated imaging;
a gearbox depending from the proximal end of the main tubular shaft, the gearbox configured for a reducing movement;
a slider mechanism configured to transmit the back and forth slider movement relative to the main tubular shaft to the gearbox;
a convergence adjustment configured to transmit to the imaging probes the back and forth slider movement after reduction by the gearbox, for causing convergence in the imaging probes;
a probe arm mechanism configured to open and close the probe arms; and
a controller configured to engage and disengage the slider mechanism and convergence adjustment, such that the back and forth slider movement after reduction by the gearbox is transmitted by the convergence adjustment to the imaging probes for convergence, and the slider mechanism and convergence adjustment each comprise at least one integrated movement element shared with the controller, the shared integrated movement element configured to assist in controlling engagement and disengagement of the slider mechanism and convergence adjustment by the controller;
inserting the distal end of the main tubular shaft through the limited access opening with the probe arms in a zero position wherein the probe arms are adjacent to one another;
using the probe arm mechanism to move the probe arms out of the zero position away from one another into an opened position between the fully closed position and a fully opened position;
adjusting the controller to permit movement of the slider after reduction by the reducing gears in the gearbox to be transmitted to the imaging probes for convergence by the convergence adjustment;
advancing the distal end of the main tubular shaft toward the target object, and thereby shortening a distance between the main tubular shaft and the target object while causing a linear movement by the slider away from the target object relative to the main tubular shaft, and causing the slider mechanism to transmit the backward linear movement to the gearbox, after which the gearbox reduces the backward linear movement by a pre-determined amount, creating a first quantity of reduced movement, the convergence adjustment thereafter transmitting the quantity of reduced movement to the imaging probes urging them toward one another to convergence on the target object while the probe arms remain in the opened position and the distal end remains at the shortened distance from the target object; and
moving the distal end away from the target object, thereby lengthening a distance from the target object, wherein the slider moves toward the target object, causing the slider mechanism to transmit the forward linear movement of the slider to the gearbox, the reducing means in the gearbox reducing the forward linear movement by a pre-determined amount to create a second quantity of reduced movement, the convergence adjustment transmitting the second quantity of reduced movement to the imaging probes such that they move away from one another and convergence on the target object while the probe arms remain in the opened position and the distal end remains at the lengthened distance from the target object.

17. The method of claim 16 comprising the steps of providing a rotatable manual convergence adjust control, associating the rotatable manual convergence adjust control with the convergence adjustment, and using the rotatable manual control to manually converge the imaging probes.

18. The method of claim 16 wherein at least one part of at least one component of the device selected from the group consisting of medical systems, non-medical systems, diagnostic systems, therapeutic systems, mechanical systems, camera systems, optical systems, light sources, different light wavelengths sensors, different light wavelengths transmitters, fiber-optic systems, light emitting diode (LED) systems, fluorescence imaging systems, ultrasound systems, magnetic resonance imaging (MRI) systems, radiation systems, radio-frequency systems, laser systems, devices using electrical power to function, devices using non-electrical forms of energy to function, distance sensors, position sensors, cautery systems, irrigation systems, anti-fogging materials, anti-smudging materials, fluid-repellant materials, scissors, graspers, clamps, handles, and forceps.

19. The method of claim 16 comprising the step of providing at least one computer component, at least one motor, and at least one positioning sensor determining endoscope-to-target distance associated with the at least two functionally identical imaging probes; the step of placing the at least one computer component in communication with the at least one positioning sensor and the at least one motor; the step of using the at least one computer component to periodically receive information from the at least one positioning sensor and determine from the received information whether a convergence correction in the functionally identical imaging probes is needed; and the step of using the at least one computer component to activate the motor when a convergence correction is needed.

20. The method of claim 16 comprising the step of providing at least one robotic system, adapting the endoscopic device to work with the at least one robotic system.

* * * * *